(12) United States Patent
Ransbury et al.

(10) Patent No.: US 7,734,343 B2
(45) Date of Patent: Jun. 8, 2010

(54) IMPLANTABLE INTRAVASCULAR DEVICE FOR DEFIBRILLATION AND/OR PACING

(75) Inventors: Terrance Ransbury, Pleasanton, CA (US); Michael S. Williams, Santa Rosa, CA (US)

(73) Assignee: Synecor, LLC, Durham, NC (US)

( * ) Notice: Subject to any disclaimer, the term of this patent is extended or adjusted under 35 U.S.C. 154(b) by 579 days.

(21) Appl. No.: 11/443,841

(22) Filed: May 31, 2006

(65) Prior Publication Data

US 2006/0224225 A1 Oct. 5, 2006

Related U.S. Application Data

(63) Continuation of application No. 10/454,223, filed on Jun. 4, 2003, now Pat. No. 7,082,336, and a continuation of application No. 10/453,971, filed on Jun. 4, 2003.

(51) Int. Cl.
*A61B 19/00* (2006.01)
*A61N 1/05* (2006.01)
*A61N 1/372* (2006.01)

(52) U.S. Cl. .............................. 607/4; 607/126; 606/129

(58) Field of Classification Search .................. 607/36, 607/1–2, 4–5, 9, 115–116, 119–120, 122–123, 607/126; 361/299.1, 299.2, 329, 749; 606/129
See application file for complete search history.

(56) References Cited

U.S. PATENT DOCUMENTS

| | | | | |
|---|---|---|---|---|
| 3,211,154 A | 10/1965 | Becker et al. | ............... | 128/421 |
| 3,236,239 A | 2/1966 | Berkovits | ................... | 128/419 |
| 3,258,013 A | 6/1966 | Druz | ....................... | 128/419 |
| 3,389,704 A | 6/1968 | Buchowski et al. | ......... | 128/419 |
| 3,835,864 A | 9/1974 | Rasor et al. | | |
| 3,865,101 A | 2/1975 | Saper et al. | ............. | 128/2.06 R |
| 3,906,960 A | 9/1975 | Lehr | ..................... | 128/419 PG |
| 3,959,706 A | 5/1976 | Mabuchi et al. | ............. | 320/103 |
| 4,025,860 A | 5/1977 | Shibata et al. | ................. | 320/3 |
| 4,030,509 A | 6/1977 | Heilman et al. | ......... | 128/419 D |
| 4,041,956 A | 8/1977 | Purdy et al. | ................... | 607/36 |
| 4,096,856 A | 6/1978 | Smith et al. | ........... | 128/4.19 D |
| 4,096,866 A | 6/1978 | Fischell | ....................... | 607/34 |
| 4,168,711 A | 9/1979 | Cannon, III et al. | ........... | 607/5 |

(Continued)

FOREIGN PATENT DOCUMENTS

EP 0 030 953 B1 7/1981

(Continued)

OTHER PUBLICATIONS

File wrapper for U.S. Appl. No. 10/454,223 (U.S. Patent No. 7,082,336).

(Continued)

*Primary Examiner*—Carl H Layno
*Assistant Examiner*—Jessica Reidel

(57) ABSTRACT

The present application describes an intravascular implantable pacing and/or defibrillation system. The described system includes a pulse generator that is implantable within a blood vessel and proportioned to blood flow through the blood vessel, and at least one lead attachable to the pulse generator. During implantation, the pulse generator is introduced into a patient's vasculature, advanced to a desired vessel and anchored in place within the vessel. The lead or leads are placed within the heart or surrounding vessels as needed to deliver electrical pulses to the appropriate location.

20 Claims, 16 Drawing Sheets

U.S. PATENT DOCUMENTS

| | | | |
|---|---|---|---|
| RE30,366 E | 8/1980 | Rasor et al. | |
| 4,323,075 A | 4/1982 | Langer | 607/5 |
| 4,326,532 A | 4/1982 | Hammar | |
| 4,332,259 A | 6/1982 | McCorkle, Jr. | 607/123 |
| 4,414,986 A | 11/1983 | Dickhudt et al. | 607/117 |
| 4,485,813 A | 12/1984 | Anderson et al. | |
| 4,510,551 A * | 4/1985 | Brainard, II | 361/684 |
| 4,530,550 A | 7/1985 | Kondo | 315/241 P |
| 4,559,951 A | 12/1985 | Dahl et al. | |
| 4,628,944 A | 12/1986 | MacGregor et al. | |
| 4,635,639 A | 1/1987 | Hakala et al. | 607/4 |
| 4,637,397 A | 1/1987 | Jones et al. | 607/5 |
| 4,662,377 A | 5/1987 | Heilman et al. | 607/4 |
| 4,687,482 A | 8/1987 | Hanson | |
| 4,708,145 A | 11/1987 | Tacker, Jr. et al. | 607/5 |
| 4,722,353 A | 2/1988 | Sluetz | 607/128 |
| 4,727,877 A | 3/1988 | Kallok | 607/5 |
| 4,736,150 A | 4/1988 | Wagner | 320/139 |
| 4,825,871 A | 5/1989 | Cansell | 607/2 |
| 4,827,936 A | 5/1989 | Pless et al. | 607/4 |
| 4,850,357 A | 7/1989 | Bach, Jr. | 607/7 |
| 4,892,102 A | 1/1990 | Astrinsky | 600/374 |
| 4,900,303 A | 2/1990 | Lemelson | |
| 4,931,947 A | 6/1990 | Werth et al. | 700/297 |
| 4,953,551 A | 9/1990 | Mehra et al. | 607/5 |
| 4,969,463 A | 11/1990 | Dahl et al. | 607/5 |
| 4,991,603 A | 2/1991 | Cohen et al. | 607/125 |
| 4,996,984 A | 3/1991 | Sweeney | 607/5 |
| 4,998,531 A | 3/1991 | Bocchi et al. | 607/5 |
| 4,998,975 A | 3/1991 | Cohen et al. | 607/5 |
| 5,010,894 A | 4/1991 | Edhag | 607/128 |
| 5,014,696 A | 5/1991 | Mehra | 607/5 |
| 5,044,375 A | 9/1991 | Bach, Jr. et al. | 607/122 |
| 5,099,838 A | 3/1992 | Bardy | 607/2 |
| 5,105,810 A | 4/1992 | Collins et al. | 607/9 |
| 5,107,834 A | 4/1992 | Ideker et al. | 607/5 |
| 5,129,392 A | 7/1992 | Bardy et al. | 607/2 |
| 5,131,388 A | 7/1992 | Pless et al. | 607/5 |
| 5,133,353 A | 7/1992 | Hauser | 607/4 |
| 5,144,946 A | 9/1992 | Weinberg et al. | 607/2 |
| 5,163,427 A | 11/1992 | Keimel | 607/5 |
| 5,170,784 A | 12/1992 | Ramon et al. | 607/9 |
| 5,170,802 A | 12/1992 | Mehra | 607/126 |
| 5,174,288 A | 12/1992 | Bardy et al. | 607/2 |
| 5,193,540 A | 3/1993 | Schulman et al. | |
| 5,199,429 A | 4/1993 | Kroll et al. | 607/5 |
| 5,221,261 A | 6/1993 | Termin et al. | 604/104 |
| 5,231,996 A | 8/1993 | Bardy et al. | 607/126 |
| 5,235,977 A | 8/1993 | Hirschberg et al. | 607/5 |
| 5,235,978 A | 8/1993 | Hirschberg et al. | 607/5 |
| 5,235,979 A | 8/1993 | Adams | 607/5 |
| 5,241,960 A | 9/1993 | Anderson et al. | 607/5 |
| 5,261,400 A | 11/1993 | Bardy | 607/5 |
| 5,282,785 A | 2/1994 | Shapland et al. | |
| 5,292,338 A | 3/1994 | Bardy | 607/5 |
| 5,306,291 A | 4/1994 | Kroll et al. | 607/5 |
| 5,314,430 A | 5/1994 | Bardy | 607/5 |
| 5,324,309 A | 6/1994 | Kallok | 607/5 |
| 5,334,221 A | 8/1994 | Bardy | 607/14 |
| 5,342,399 A | 8/1994 | Kroll | 607/5 |
| 5,356,425 A | 10/1994 | Bardy et al. | 607/14 |
| 5,358,514 A | 10/1994 | Schulman et al. | |
| 5,368,588 A | 11/1994 | Bettinger | |
| 5,372,585 A | 12/1994 | Tiefenbrun et al. | |
| 5,383,907 A | 1/1995 | Kroll | 607/5 |
| 5,407,444 A | 4/1995 | Kroll | 607/5 |
| 5,411,546 A | 5/1995 | Bowald et al. | 607/126 |
| 5,423,865 A | 6/1995 | Bowald et al. | 607/5 |
| 5,423,885 A | 6/1995 | Williams | |
| 5,431,686 A | 7/1995 | Kroll et al. | 607/7 |
| 5,468,254 A | 11/1995 | Hahn et al. | 607/5 |
| 5,483,165 A | 1/1996 | Cameron et al. | 324/427 |
| 5,487,760 A | 1/1996 | Villafana | |
| 5,509,411 A | 4/1996 | Littmann et al. | 600/381 |
| 5,531,779 A | 7/1996 | Dahl et al. | |
| 5,534,015 A | 7/1996 | Kroll et al. | 607/7 |
| 5,545,205 A | 8/1996 | Schulte et al. | 607/123 |
| 5,551,954 A | 9/1996 | Buscemi et al. | |
| 5,591,211 A | 1/1997 | Meltzer | 607/5 |
| 5,591,213 A | 1/1997 | Morgan | 607/5 |
| 5,593,427 A | 1/1997 | Gliner et al. | 607/7 |
| 5,593,434 A | 1/1997 | Williams | |
| 5,601,612 A | 2/1997 | Gliner et al. | 607/7 |
| 5,607,454 A | 3/1997 | Cameron et al. | 607/5 |
| 5,613,935 A | 3/1997 | Jarvik | |
| 5,617,853 A | 4/1997 | Morgan | 600/386 |
| 5,620,470 A | 4/1997 | Gliner et al. | 607/7 |
| 5,645,586 A | 7/1997 | Meltzer | |
| 5,699,796 A | 12/1997 | Littmann et al. | 600/374 |
| 5,704,910 A | 1/1998 | Humes | |
| 5,716,391 A | 2/1998 | Grandjean | |
| 5,735,879 A | 4/1998 | Gliner et al. | 607/7 |
| 5,735,887 A | 4/1998 | Barreras, Sr. et al. | |
| 5,735,897 A | 4/1998 | Buirge | |
| 5,749,904 A | 5/1998 | Gliner et al. | 607/7 |
| 5,749,905 A | 5/1998 | Gliner et al. | 607/7 |
| 5,769,077 A | 6/1998 | Lindegren | |
| 5,776,166 A | 7/1998 | Gliner et al. | 607/7 |
| 5,800,460 A | 9/1998 | Powers et al. | 607/5 |
| 5,803,927 A | 9/1998 | Cameron et al. | 607/5 |
| 5,807,399 A | 9/1998 | Laske et al. | |
| 5,814,089 A | 9/1998 | Stokes et al. | 607/32 |
| 5,827,326 A | 10/1998 | Kroll et al. | 607/5 |
| 5,833,603 A | 11/1998 | Kovacs et al. | |
| 5,836,978 A | 11/1998 | Gliner et al. | 607/7 |
| 5,843,132 A | 12/1998 | Ilvento | 607/10 |
| 5,849,033 A | 12/1998 | Mehmanesh et al. | |
| 5,868,792 A | 2/1999 | Ochs et al. | 607/5 |
| 5,879,374 A | 3/1999 | Powers et al. | 607/5 |
| 5,891,046 A | 4/1999 | Cyrus et al. | 600/510 |
| 5,891,049 A | 4/1999 | Cyrus et al. | 600/523 |
| 5,904,707 A | 5/1999 | Ochs et al. | 607/6 |
| 5,908,447 A | 6/1999 | Schroeppel et al. | |
| 5,911,704 A | 6/1999 | Humes | |
| 5,919,210 A | 7/1999 | Lurie et al. | |
| 5,951,485 A | 9/1999 | Cyrus et al. | 600/523 |
| 5,954,761 A | 9/1999 | Machek et al. | |
| 5,957,842 A | 9/1999 | Littmann et al. | 600/381 |
| 5,957,956 A | 9/1999 | Kroll et al. | 607/5 |
| 6,016,059 A | 1/2000 | Morgan | 324/556 |
| 6,045,568 A | 4/2000 | Igaki et al. | |
| 6,047,212 A | 4/2000 | Gliner et al. | 607/7 |
| 6,053,873 A | 4/2000 | Govari et al. | |
| 6,088,610 A | 7/2000 | Littmann et al. | 600/381 |
| 6,119,039 A | 9/2000 | Leyde | 607/5 |
| 6,141,576 A | 10/2000 | Littmann et al. | 600/381 |
| 6,141,588 A | 10/2000 | Cox et al. | 607/9 |
| 6,161,029 A | 12/2000 | Spreigl et al. | 600/381 |
| 6,214,032 B1 | 4/2001 | Loeb et al. | |
| 6,219,581 B1 | 4/2001 | Schaldach et al. | 607/122 |
| 6,230,061 B1 | 5/2001 | Hartung | 607/122 |
| 6,231,516 B1 | 5/2001 | Keilman et al. | |
| 6,256,534 B1 | 7/2001 | Dahl | 607/5 |
| 6,256,541 B1 | 7/2001 | Heil et al. | |
| 6,304,786 B1 | 10/2001 | Heil, Jr. et al. | |
| 6,330,481 B1 | 12/2001 | Van Wijk et al. | |
| 6,383,171 B1 | 5/2002 | Gifford et al. | |
| 6,419,692 B1 | 7/2002 | Yang et al. | 623/1.15 |
| 6,436,068 B1 | 8/2002 | Bardy | 604/57 |
| 6,442,413 B1 | 8/2002 | Silver | 600/345 |
| 6,445,953 B1 | 9/2002 | Bulkes et al. | |
| 6,509,104 B2 | 1/2003 | Huang et al. | |
| 6,516,231 B1 | 2/2003 | Flammang | 607/122 |
| 6,522,926 B1 | 2/2003 | Kieval et al. | |

| Patent Number | Date | Inventor | Class |
|---|---|---|---|
| 6,561,975 B1 | 5/2003 | Pool et al. | 600/300 |
| 6,564,807 B1 | 5/2003 | Schulman et al. | |
| 6,572,605 B1 | 6/2003 | Humes | |
| 6,584,362 B1 | 6/2003 | Scheiner et al. | 607/122 |
| 6,671,547 B2 | 12/2003 | Lyster et al. | 607/6 |
| 6,716,208 B2 | 4/2004 | Humes | |
| 6,723,121 B1 | 4/2004 | Zhong | |
| 6,726,714 B2 | 4/2004 | DiCaprio et al. | |
| 6,733,485 B1 | 5/2004 | Whitehurst et al. | 604/500 |
| 6,735,474 B1 | 5/2004 | Loeb et al. | 607/41 |
| 6,735,475 B1 | 5/2004 | Whitehurst et al. | |
| 6,754,528 B2 | 6/2004 | Bardy et al. | 607/5 |
| 6,760,622 B2 | 7/2004 | Helland et al. | 607/9 |
| 6,776,784 B2 | 8/2004 | Ginn | 606/151 |
| 6,778,860 B2 | 8/2004 | Ostroff et al. | 607/7 |
| 6,783,499 B2 | 8/2004 | Schwartz | |
| 6,783,543 B2 | 8/2004 | Jang | |
| 6,788,974 B2 | 9/2004 | Bardy et al. | 607/36 |
| 6,829,504 B1 | 12/2004 | Chen et al. | |
| 6,834,204 B2 | 12/2004 | Ostroff et al. | 607/2 |
| 6,845,267 B2 | 1/2005 | Harrison et al. | |
| 6,866,044 B2 | 3/2005 | Bardy et al. | 128/898 |
| 6,885,895 B1 | 4/2005 | Whitehurst et al. | 607/39 |
| 6,907,285 B2 | 6/2005 | Denker et al. | 607/5 |
| 6,932,930 B2 | 8/2005 | DeSimone et al. | |
| 6,933,822 B2 | 8/2005 | Haugs et al. | |
| 6,941,169 B2 * | 9/2005 | Pappu | 607/9 |
| 7,003,350 B2 | 2/2006 | Denker et al. | |
| 7,006,858 B2 | 2/2006 | Silver et al. | |
| 7,054,692 B1 | 5/2006 | Whitehurst et al. | |
| 7,072,171 B1 | 7/2006 | Muffoletto et al. | |
| 7,082,336 B2 | 7/2006 | Ransbury et al. | |
| 7,097,665 B2 | 8/2006 | Stack et al. | |
| 7,114,502 B2 | 10/2006 | Schulman et al. | |
| 7,236,821 B2 | 6/2007 | Cates et al. | |
| 7,239,921 B2 | 7/2007 | Canfield et al. | |
| 7,529,589 B2 | 5/2009 | Williams et al. | |
| 2001/0021840 A1 | 9/2001 | Suresh et al. | |
| 2001/0041930 A1 | 11/2001 | Globerman et al. | |
| 2002/0026228 A1 | 2/2002 | Schauerte | 607/122 |
| 2002/0042630 A1 | 4/2002 | Bardy et al. | 607/5 |
| 2002/0042634 A1 | 4/2002 | Bardy et al. | 607/36 |
| 2002/0052636 A1 | 5/2002 | Bardy et al. | 607/129 |
| 2002/0072773 A1 | 6/2002 | Bardy et al. | 607/5 |
| 2002/0090388 A1 | 7/2002 | Humes et al. | |
| 2002/0090389 A1 | 7/2002 | Humes et al. | 424/422 |
| 2002/0103510 A1 | 8/2002 | Bardy et al. | 607/5 |
| 2002/0107545 A1 | 8/2002 | Rissmann et al. | 607/5 |
| 2002/0107546 A1 | 8/2002 | Ostroff et al. | 607/4 |
| 2002/0107547 A1 | 8/2002 | Erlinger et al. | 607/5 |
| 2002/0107548 A1 | 8/2002 | Bardy et al. | 607/5 |
| 2002/0107549 A1 | 8/2002 | Bardy et al. | 607/5 |
| 2002/0107559 A1 | 8/2002 | Sanders et al. | 607/129 |
| 2002/0111585 A1 | 8/2002 | Lafontaine | |
| 2002/0120299 A1 | 8/2002 | Ostroff et al. | 607/5 |
| 2002/0128546 A1 | 9/2002 | Silver | |
| 2002/0133224 A1 | 9/2002 | Bajgar et al. | 623/1.39 |
| 2002/0143379 A1 | 10/2002 | Morgan et al. | |
| 2002/0147486 A1 | 10/2002 | Soukup et al. | |
| 2002/0183791 A1 | 12/2002 | Denker et al. | 607/5 |
| 2002/0188252 A1 | 12/2002 | Bardy | 604/93.01 |
| 2003/0023177 A1 | 1/2003 | Bardy | 600/510 |
| 2003/0032892 A1 | 2/2003 | Erlach et al. | 600/547 |
| 2003/0032998 A1 | 2/2003 | Altman | |
| 2003/0036778 A1 | 2/2003 | Ostroff et al. | 607/9 |
| 2003/0045904 A1 | 3/2003 | Bardy et al. | 607/4 |
| 2003/0060863 A1 | 3/2003 | Dobak, III | |
| 2003/0088278 A1 | 5/2003 | Bardy et al. | 607/5 |
| 2003/0097051 A1 | 5/2003 | Kolberg et al. | 600/381 |
| 2003/0114905 A1 | 6/2003 | Kuzma | |
| 2003/0158584 A1 | 8/2003 | Cates et al. | 607/2 |
| 2004/0073190 A1 | 4/2004 | Deem et al. | |
| 2004/0116992 A1 | 6/2004 | Wardle et al. | |
| 2004/0147993 A1 | 7/2004 | Westlund et al. | |
| 2004/0172090 A1 | 9/2004 | Janzig et al. | |
| 2004/0207503 A1 | 10/2004 | Flanders et al. | |
| 2004/0249417 A1 | 12/2004 | Ransbury et al. | |
| 2004/0249431 A1 | 12/2004 | Ransbury et al. | |
| 2005/0004639 A1 | 1/2005 | Erickson | |
| 2005/0019370 A1 | 1/2005 | Humes | |
| 2005/0043765 A1 | 2/2005 | Williams et al. | |
| 2005/0043789 A1 | 2/2005 | Widenhouse et al. | |
| 2005/0080472 A1 | 4/2005 | Atkinson et al. | 607/126 |
| 2005/0119718 A1 | 6/2005 | Coe et al. | |
| 2005/0147647 A1 | 7/2005 | Glauser et al. | |
| 2005/0228471 A1 | 10/2005 | Williams et al. | |
| 2005/0234431 A1 | 10/2005 | Williams et al. | |
| 2006/0095078 A1 | 5/2006 | Tronnes | |
| 2006/0129050 A1 | 6/2006 | Martinson et al. | |
| 2006/0224225 A1 | 10/2006 | Ransbury et al. | |
| 2006/0241732 A1 | 10/2006 | Denker et al. | |
| 2008/0077219 A1 | 3/2008 | Williams et al. | |

FOREIGN PATENT DOCUMENTS

| | | |
|---|---|---|
| EP | 0 057 448 B1 | 8/1982 |
| EP | 0 281 219 B1 | 9/1988 |
| EP | 0 373 953 A2 | 6/1990 |
| EP | 0 373 953 A3 | 6/1990 |
| EP | 0 424 379 B1 | 5/1991 |
| EP | 0 426 089 A2 | 5/1991 |
| EP | 0 426 089 A3 | 5/1991 |
| EP | 0 453 761 A1 | 10/1991 |
| EP | 0 526 671 A1 | 2/1993 |
| EP | 0 526 671 B1 | 2/1993 |
| EP | 0 559 932 A1 | 9/1993 |
| EP | 0 559 933 A1 | 9/1993 |
| EP | 0 570 712 A1 | 11/1993 |
| EP | 0 570 712 B1 | 11/1993 |
| EP | 0 578 748 B1 | 1/1994 |
| EP | 0 601 338 A1 | 6/1994 |
| EP | 0 601 338 B1 | 6/1994 |
| EP | 0 601 338 B2 | 6/1994 |
| EP | 0 601 339 B1 | 6/1994 |
| EP | 0 601 340 A1 | 6/1994 |
| EP | 0 601 340 B1 | 6/1994 |
| EP | 0 646 391 A1 | 4/1995 |
| EP | 0 646 391 B1 | 4/1995 |
| EP | 0 669 839 B2 | 9/1995 |
| EP | 0 799 628 A3 | 4/1996 |
| EP | 0 779 080 B1 | 6/1997 |
| EP | 0 799 628 A2 | 10/1997 |
| EP | 0 813 886 A2 | 12/1997 |
| EP | 0 892 653 B1 | 1/1999 |
| EP | 1 106 202 A2 | 6/2001 |
| EP | 1 106 202 A3 | 3/2004 |
| EP | 0 813 886 A3 | 9/2004 |
| EP | 0 813 886 B1 | 9/2004 |
| GB | 2 157 178 A | 10/1985 |
| WO | WO 92/11898 | 7/1992 |
| WO | WO 92/17240 | 10/1992 |
| WO | WO 92/20401 | 11/1992 |
| WO | WO 94/07564 | 4/1994 |
| WO | WO 96/39098 | 12/1996 |
| WO | WO 97/31678 | 9/1997 |
| WO | WO 98/52641 | 11/1998 |
| WO | WO 99/34731 | 7/1999 |
| WO | WO 00/74557 A1 | 12/2000 |
| WO | WO 02/15824 A3 | 2/2002 |
| WO | WO 02/22208 | 3/2002 |
| WO | WO 02/055136 A2 | 7/2002 |
| WO | WO 02/056796 A1 | 7/2002 |
| WO | WO 02/064206 A2 | 8/2002 |
| WO | WO 2004/004603 A1 | 1/2004 |
| WO | WO 2004/028348 A2 | 4/2004 |
| WO | WO 2004/049919 A2 | 6/2004 |

| | | |
|---|---|---|
| WO | WO 2004/058100 A2 | 7/2004 |
| WO | WO 2005/000398 A2 | 1/2005 |

OTHER PUBLICATIONS

File wrapper for U.S. Appl. No. 10/453,971 (U.S. Publication No. 2004/0249431).

File wrapper for U.S. Appl. No. 11/980,006 (U.S. Publication No. 2008/0077219).

File wrapper for U.S. Appl. No. 10/977,060 (U.S. Publication No. 2005/0228471).

File wrapper for U.S. Appl. No. 12/506,232 (U.S. Publication No. 2009/0281521).

File wrapper for U.S. Appl. No. 10/862,113 (U.S. Patent No. 7,529,589).

* cited by examiner

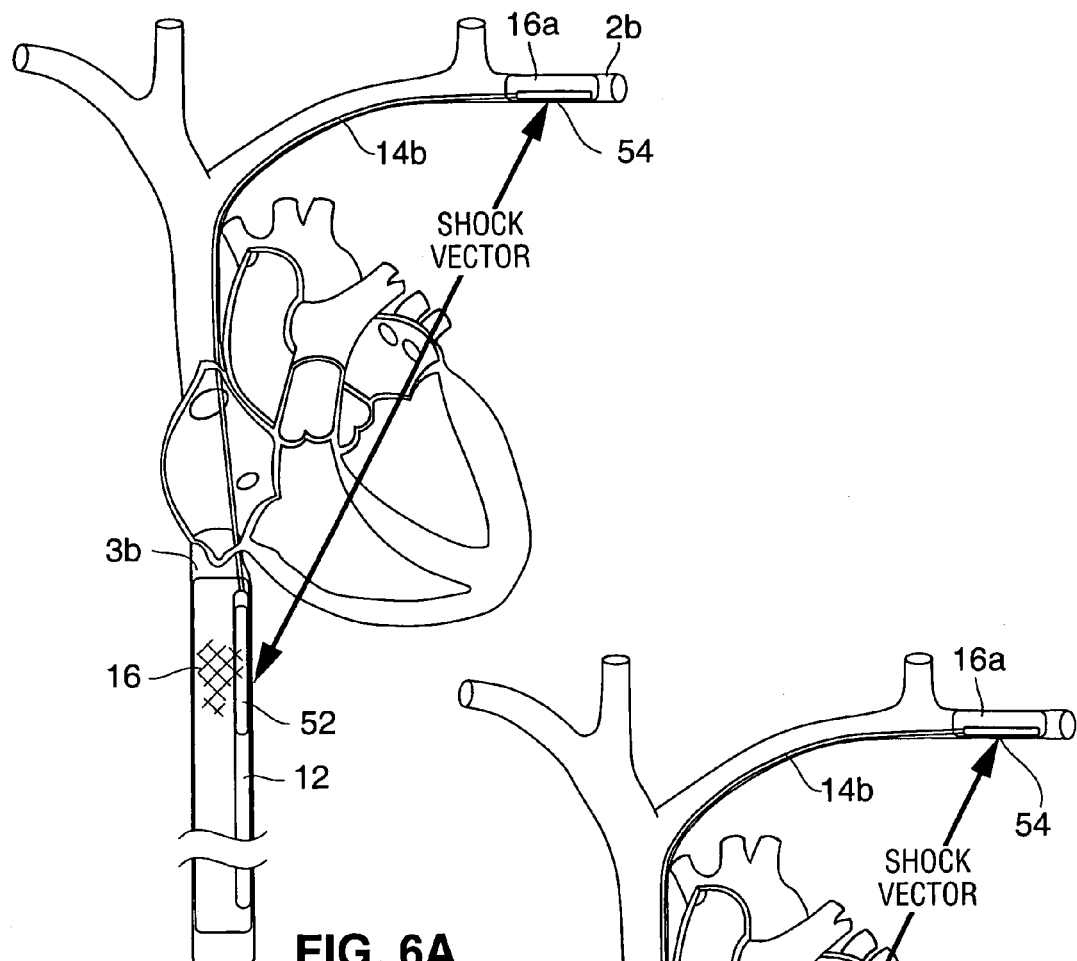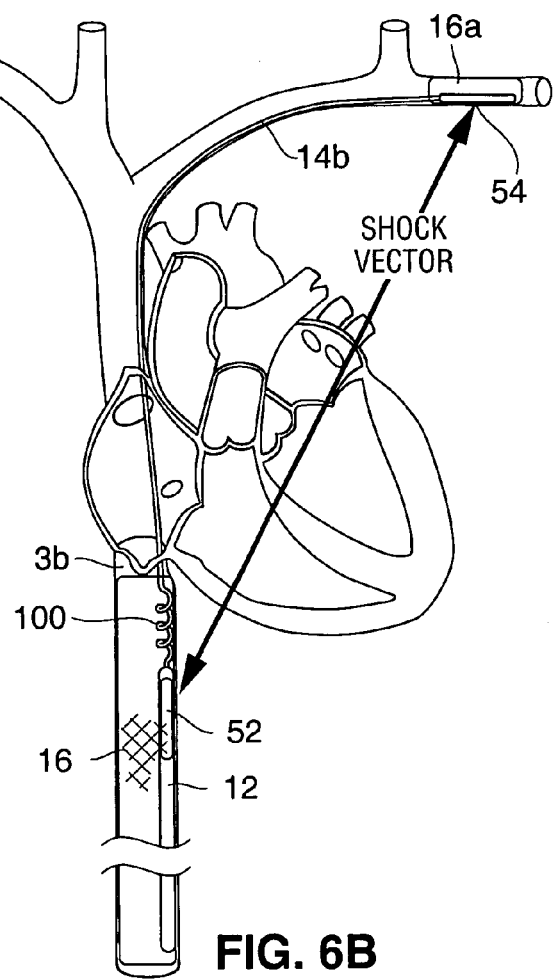
FIG. 6A
FIG. 6B

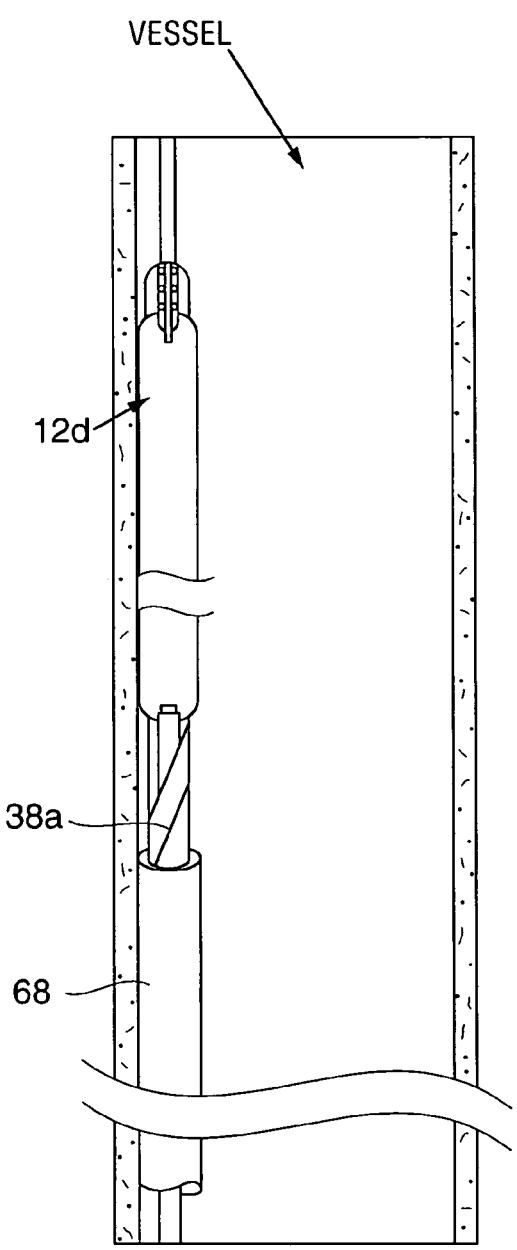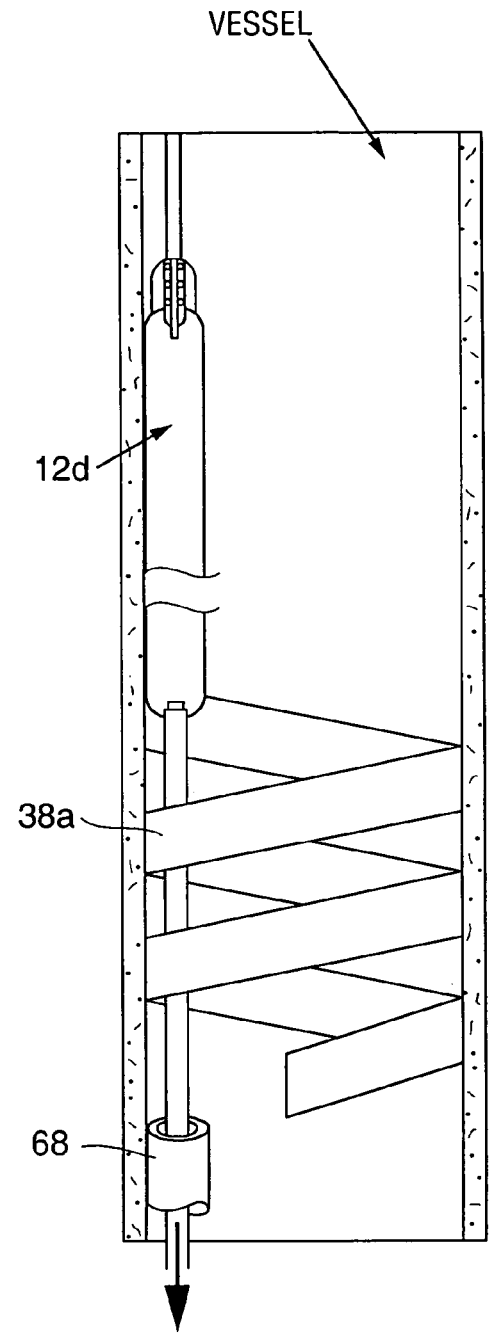
FIG. 13A  FIG. 13B

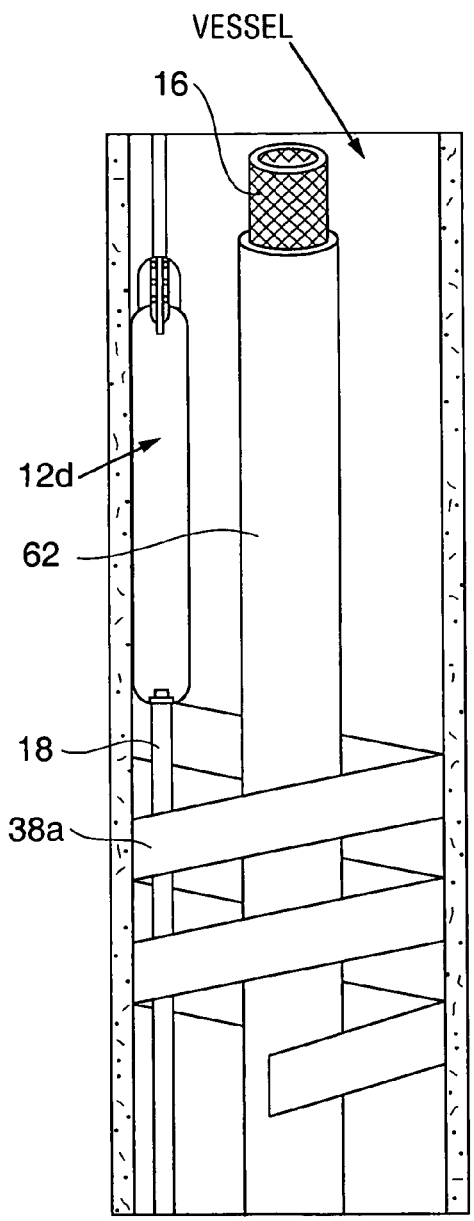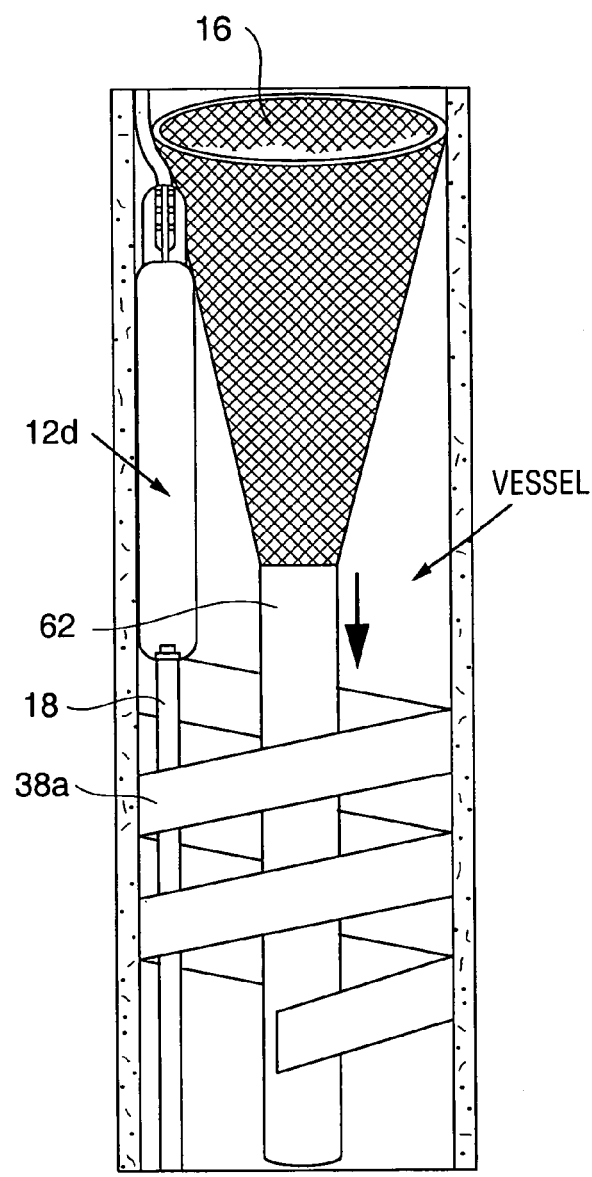
FIG. 14  FIG. 15

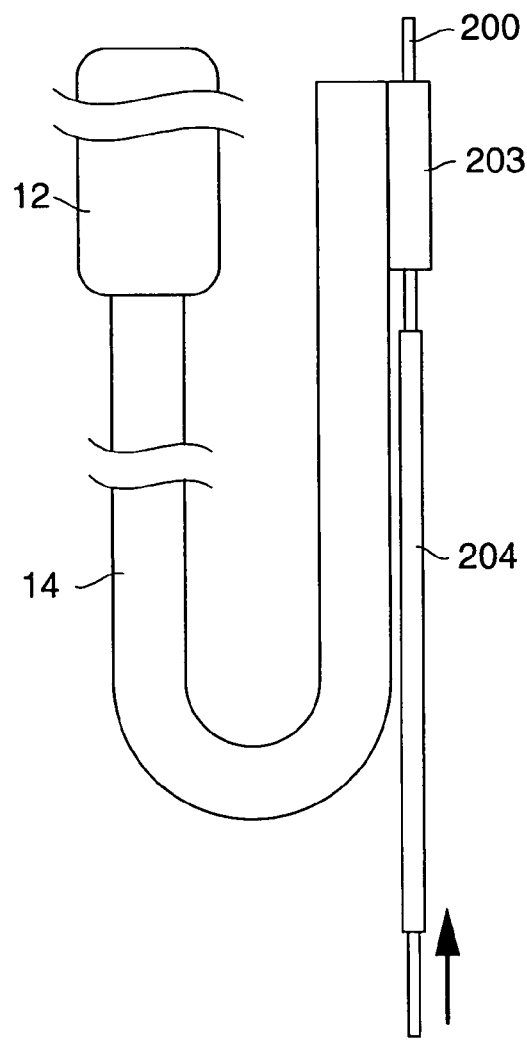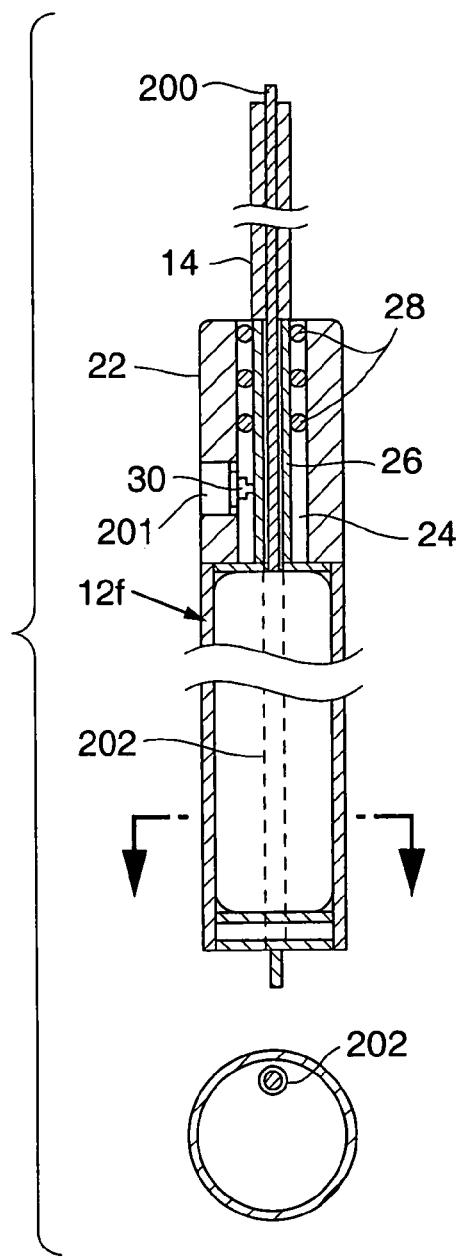
FIG. 18A
FIG. 18B

IMPLANTABLE INTRAVASCULAR DEVICE FOR DEFIBRILLATION AND/OR PACING

This is a continuation of U.S. application Ser. No. 10/454,223, filed Jun. 4, 2003 and now issued as U.S. Pat. No. 7,082,336, and a continuation of U.S. application Ser. No. 10/453,971, filed Jun. 4, 2003.

FIELD OF THE INVENTION

The present invention generally relates to devices, systems, and methods for diagnosing and treating the heart. In particular, the invention provides methods and systems for implanting medical devices into the patient's vasculature and using the devices for sensing electrical activity and/or electrically stimulating the heart

BACKGROUND OF THE INVENTION

Pacemakers and implanted cardioverter defibrillators ("ICDs") have been successfully implanted for years for treatment of heart rhythm conditions.

Pacemakers are implanted in patients who have bradycardia (slow heart rate). The pacemakers detect periods of bradycardia and deliver electrical stimuli to increase the heart beat to an appropriate rate.

ICDs are implanted in patients who may suffer from episodes of fast and irregular heart rhythms called tachyarrhythmias. ICDs come in two forms: the first type is a defibrillator for patients who may suffer ventricular fibrillation (VF), a fast and irregular heart rhythm in the ventricles. During a VF episode, the heart quivers and can pump little or no blood to the body, potentially causing sudden death. An ICD implanted for correction of ventricular fibrillation will detect a VF episode and deliver an electrical shock to the heart to restore the heart's electrical coordination.

The second type of ICD is a cardioverter for patients who may suffer from atrial fibrillation (AF), which is a loss of electrical coordination in the heart's upper chambers (atria). During AF, blood in the atria may pool and clot, placing the patient at risk for stroke. An ICD implanted for correction of atrial fibrillation will detect an AF episode and deliver an electrical shock to the atria to restore electrical coordination.

Pacemakers and ICDs are routinely implanted in the pectoral region either under the skin (subcutaneous) or under the pectoral muscle. The leads are placed at appropriate locations within or on the heart. Because of this complexity, a cardiologist identifying a heart rhythm condition may be required to refer his or her patient to sub-specialists or surgeons for implantation of a pacemaker or ICD—thus delaying implantation of the device in a patient who urgently needs it. It is thus desirable to simplify these devices and the procedures for implanting them so as to permit their implantation by a broader range of physicians.

SUMMARY OF THE INVENTION

The present application describes an intravascular implantable pacing and/or defibrillation system. The described system includes a pulse generator that is implantable within a blood vessel and proportioned to allow normal blood flow through the blood vessel, and at least one lead attachable to the pulse generator. During implantation, the pulse generator is introduced into a patient's vasculature, advanced to a desired vessel and anchored in place within the vessel. The lead or leads are placed within the heart or surrounding vessels as needed to deliver electrical pulses to the appropriate location.

BRIEF DESCRIPTION OF THE DRAWINGS

FIG. 6A schematically illustrates a first application of an intravascular defibrillation and/or pacing system.

FIG. 6B is a schematic illustration similar to FIG. 6A showing an alternative lead which includes a coiled section.

FIGS. 13A through 17 are a sequence of drawings illustrating deployment of the intravascular defibrillation and/or pacing device of FIG. 4A.

FIG. 18A is a plan view of a device similar to the devices of FIGS. 3A-4B but slightly modified to include a cuff on the lead for receiving a guidewire.

FIG. 18B is a plan view of a device similar to the devices of FIGS. 3A-4B but slightly modified to include a bore in the device for receiving a guidewire.

DETAILED DESCRIPTION OF THE DRAWINGS

Cardiac Anatomy

Figure 1:
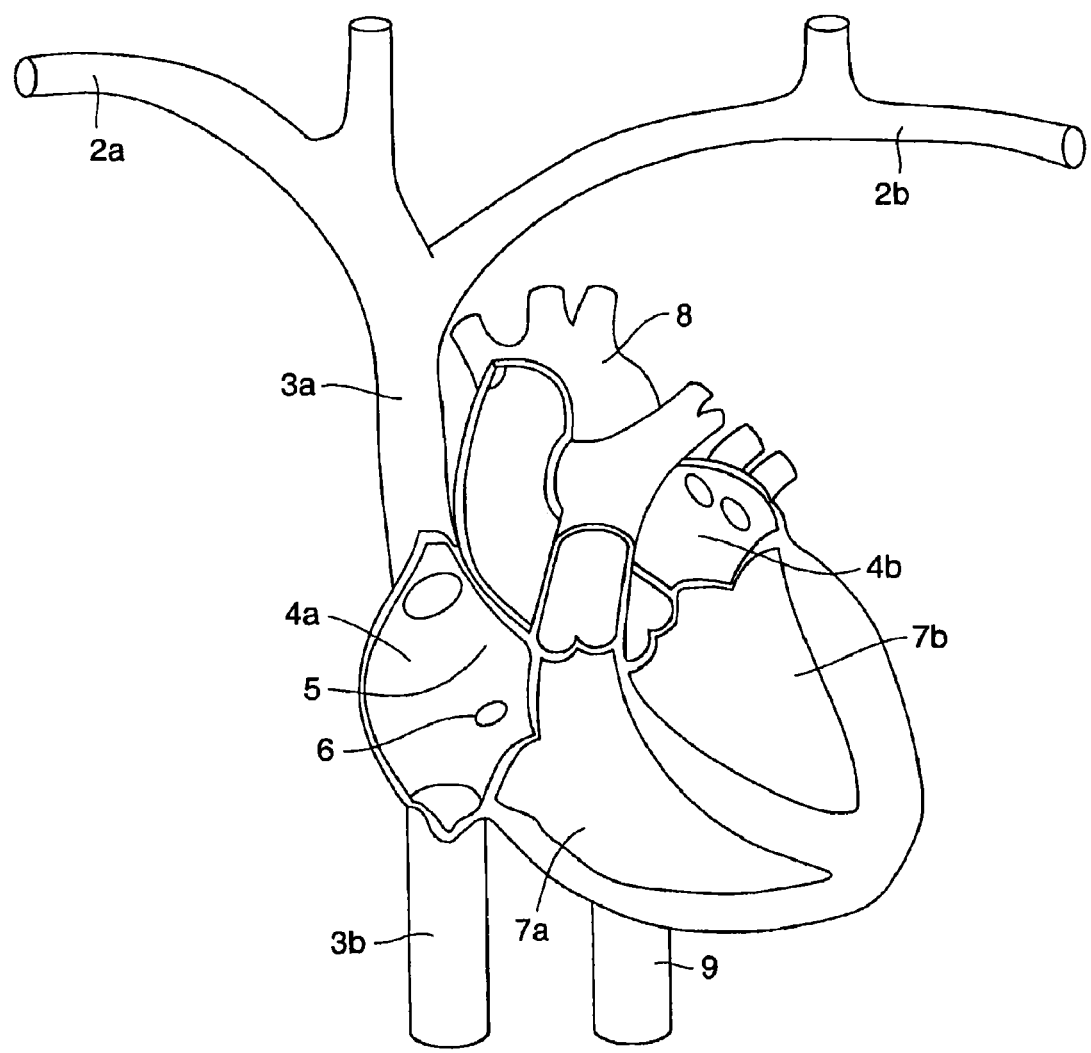
FIG. 1 is a perspective illustration showing human cardiac anatomy.

FIG. 1 shows the cardiac anatomy of a human, including the heart and major vessels. The following anatomic locations are shown and identified by the listed reference numerals:

| | |
|---|---|
| Right Subclavian | 2a |
| Left Subclavian | 2b |
| Superior Vena Cava (SVC) | 3a |
| Inferior Vena Cava (IVC) | 3b |
| Right Atrium (RA) | 4a |
| Left Atrium (LA) | 4b |
| Right Atrial Appendage (RAA) | 5 |
| Coronary Sinus Ostium (CS Os) | 6 |
| Right Ventricle (RV) | 7a |
| Left Ventricle (LV) | 7b |
| Aortic Arch | 8 |
| Descending Aorta | 9 |

System Components

Figure 2:
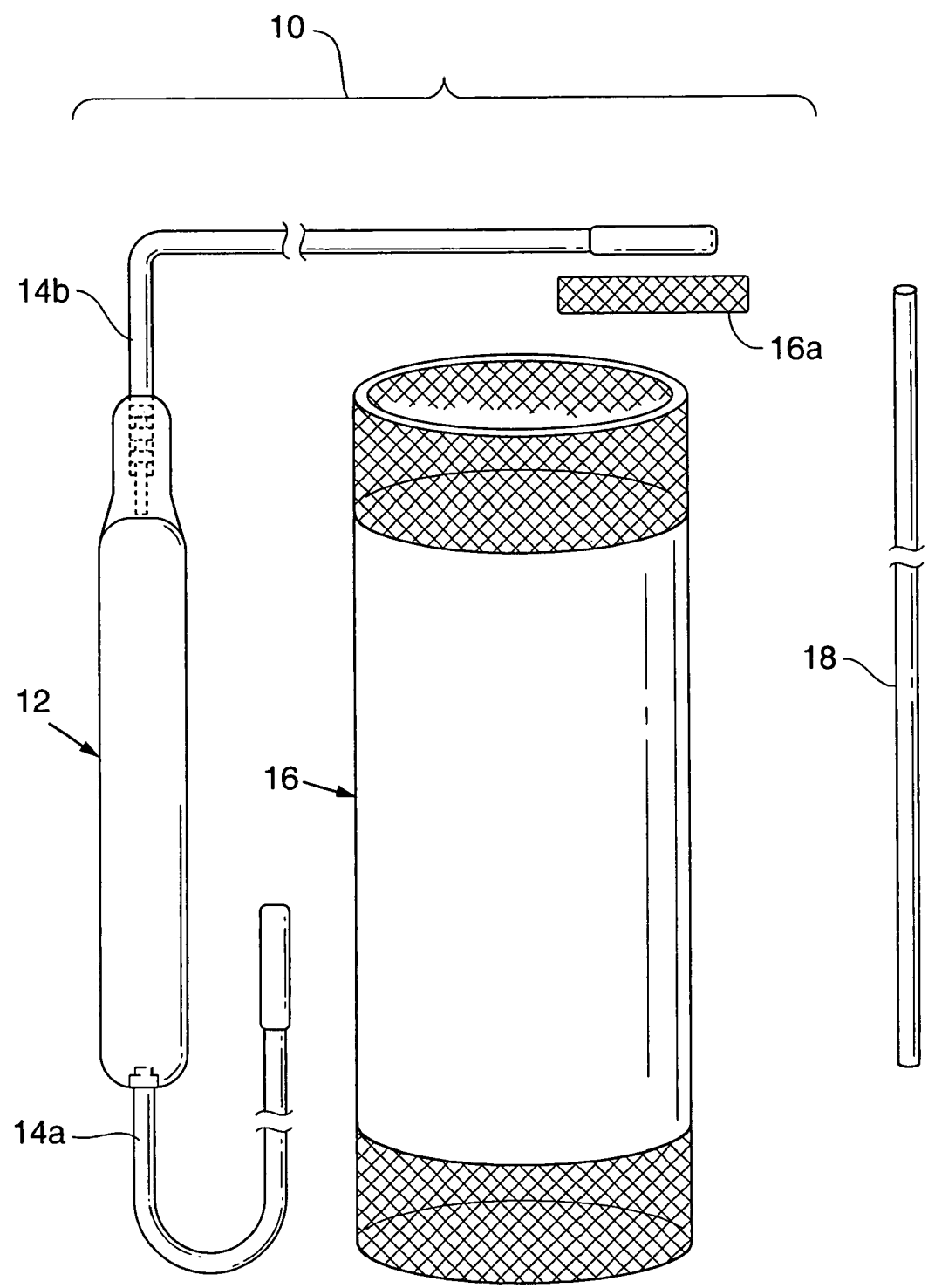
FIG. 2 is a plan view generally showing components of one form of intravascular defibrillation and/or pacing system.

FIG. 2 generally shows components that may be provided with an intravascular defibrillation and/or pacing system 10. The elements of such a system 10 may include defibrillation and/or pacing device 12, one or more leads 14a, 14b, retention devices 16, 16a, and positioning mandrel 18. It should be understood that certain of these elements may be eliminated, or others added to the system, without departing from the spirit of the invention.

Various examples of devices and leads will be given in this description. In those examples, reference numerals such as 12a, 12b, 12c etc will be used to describe certain embodiments of the device, whereas elsewhere the numeral 12 may be used to more generally refer to devices of the type which may be used with the system 10. Likewise, reference number 14 may be used generally to refer to leads of a type that may be used with the system.

Device 12 includes components known in the art to be necessary to carry out the system functions. For example, device 12 may include one or more pulse generators, including associated batteries, capacitors, microprocessors, and circuitry for generating defibrillation and/or pacing pulses. Device also includes detection circuitry for detecting arrhythmias or other abnormal activity of the heart. The specific components to be provided in the device will depend upon the application for the device, and specifically whether the device is intended to perform defibrillation, and/or pacing along with its sensing functions.

The device 12 is proportioned to be passed into the vasculature (for example into the venous system through the right or left femoral vein or the subclavian, or into the arterial system through one of the femoral arteries), and to be anchored within the patient's vasculature with minimal obstruction to blood flow. Thus, the housing of device 12 preferably has a streamlined cross section which may be in the range of 3-10 mm or less, with a most preferred cross-section of 3-7 mm or less. The cross-section of the device (transecting the longitudinal axis) may have a circular cross-section, although other cross-sections including crescent, flattened, or elliptical cross-sections may also be used.

Given the minimal space allowed for components, it is desirable to arrange the device components so as to make efficient use of the available space. Examples of devices having space efficient arrangements of their contents are shown in FIGS. 3A, 3B, 3C, 4A and 4B. One example is identified by reference numeral 12a in FIG. 3A. Device 12a includes an elongate enclosure 20 shown in cross-section in FIG. 3A to allow the components housed within it to be seen. Enclosure 20 is a rigid or semi-rigid housing preferably formed of a material that is conductive, biocompatible, capable of sterilization and capable of hermetically sealing the components contained within the enclosure 20. One example of such a material is titanium, although other materials may also be used.

The housing is preferably covered by an electrically insulative layer or coating 21 such as ePTFE. It is desirable to provide a coating that is anti-thrombogenic (e.g. perfluorocarbon coatings applied using supercritical carbon dioxide) so as to prevent thrombus formation on the device. It is also beneficial that the coating have anti-proliferative properties so as to minimize endothelialization or cellular ingrowth, since minimizing growth into or onto the device will help minimize vascular trauma when the device is explanted. The coating may thus also be one which elutes anti-thrombogenic compositions (e.g. heparin sulfate) and/or compositions that inhibit cellular ingrowth and/or immunosuppressive agents. As will be described below in connection with FIG. 6A, this layer or coating may be selectively applied or removed to leave an exposed electrode region 52 on the surface of the enclosure 20.

One or more leads extend from device 12a. In the FIG. 3A embodiment a single lead 14b is shown, although the device may include a defibrillation lead 14b, a pacing lead 14a, or both as shown in FIG. 2. If two leads are used, they may extend from opposite ends of the device as shown in FIG. 2, or they may extend from the same end of the device. Either or both of the leads may be equipped to sense electrical activity of the heart. Monitoring of the heart's electrical activity is needed to detect the onset of an arrhythmia. Activity sensed by the sensing electrode(s) is used by the device electronics to trigger delivery of a defibrillation shock via lead 14b or a pacing impulse via a pacing lead (such as lead 14a of FIG. 2).

The leads 14a, 14b may be conventional defibrillation/pacing leads, although alternative lead configurations may be desirable if warranted by the desired placement of the device 12a and leads within the body. For example, the physician will preferably want to select a location for the device within a chosen vessel (i.e. the inferior or superior vena cava) that will prevent the device from blocking significant peripheral vessels extending from that vessel. Optimal leads will preferably give the physician implanting the device flexibility to position the device at an appropriate location in the chosen vessel without concern that the leads extending from the device will not reach their intended location. Thus, for some patients it may be necessary to use a lead that is slightly longer than conventional leads, or the lead may include a coiled section 100 (FIG. 6B) that is similar to the configuration of a coiled telephone cord. Coiled section 100 allows elongation of the effective length of the lead when tension is applied to the coil. Other configurations that will allow additional lead length to pay out from the device if needed may also be used.

For leads that are to be positioned within a chamber of the heart, the leads may be the screw-in or tined variety for fixation to the cardiac tissue, or they may have steroid-eluding tips to facilitate tissue in-growth for fixation purposes.

The leads may include non-thrombogenic and/or non-proliferative surfaces or coatings as also described above in connection with the device 12.

Figure 3A:
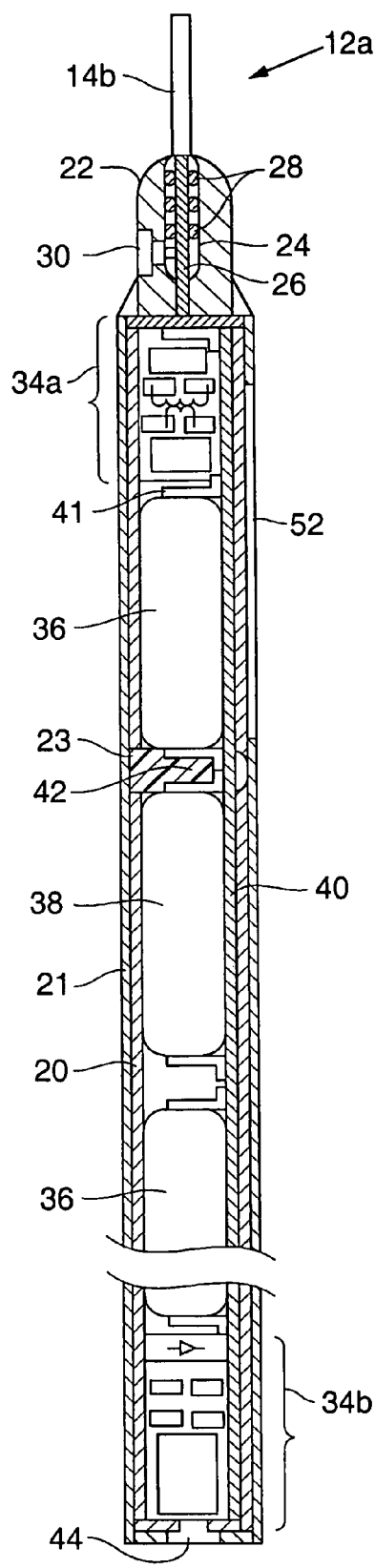
FIG. 3A is a plan view showing a first embodiment of an intravascular defibrillation and/or pacing device of a type which may be used with the system shown in FIG. 2.

The leads 14a, 14b may be permanently or temporarily attached to the device 12a. FIG. 3A illustrates one means for detachably connecting a lead to the device 12a. In this embodiment, device 12a includes a header 22 having a socket 24. To attach lead 14b to the device 12a, a pin 26 at the proximal end of lead 14b is inserted into socket 24. A series of o-ring seals 28 surround the pin 26 within the socket 24 to prevent body fluids from passing into the device 12a. A set screw 30 tightens against the pin 26 to secure the pin within the socket.

Within the enclosure 20 are the electronic components 34a, 34b that govern operation of the device 12a. For example, in the FIG. 3A embodiment, components 34a are associated with delivery of a defibrillation pulse via lead 14b, whereas components 32b are associated with the sensing function performed using sensing electrodes on the defibrillation lead or on a separate lead (not shown). Isolating components 34a from components 34b may be desirable if noise generated by the high voltage defibrillation circuitry 34a during charging might interfere with performance of the sensing circuitry 34b.

Device 12a further includes one or more batteries 36 for supplying power to the device, and one or more capacitors 38 for storing an electrical charge and for delivering stored charge to the defibrillation lead(s) 14b and/or exposed electrode 52 on the enclosure 20. A circuit interconnect 40 provides the electrical coupling between the electronic components 34a, 34b, lead 14b, electrode 52, batteries 36 and capacitors 38. Contacts 41 couple these components to the interconnect 40.

As shown in FIG. 3A, the components of device 12a may be arranged in series with one another to give the device 12a a streamlined profile. Because the device 12a is intended for implantation within the patient's vasculature, some flexibility may be desired so as to allow the elongate device to be easily passed through the vasculature. Flexibility may be added by segmenting the device, such as by forming one or more breaks 23 in the enclosure 20, and by forming one or more hinge zones 42 at each break 23 by connecting the segments using silicone rubber filler. The hinge zones 42 thus form living hinges, which bend in response to passage of the device 12a though curved regions of the vasculature. It should be noted that in this embodiment it is desirable to form interconnect 40 as a flex circuit so that it will not prevent bending at the hinge zones.

A proximal portion of the device 12a may include a connector 44 for receiving the distal end of positioning mandrel 18 (FIG. 2), which may optionally be used to push the device 12a through the patient's vasculature as described below. The connector 44 may take the form of a threaded bore for receiving a threaded screw member at the distal end of the mandrel 18, or it may have any other type of configuration for detachably engaging the distal end of the mandrel.

Figure 3B:
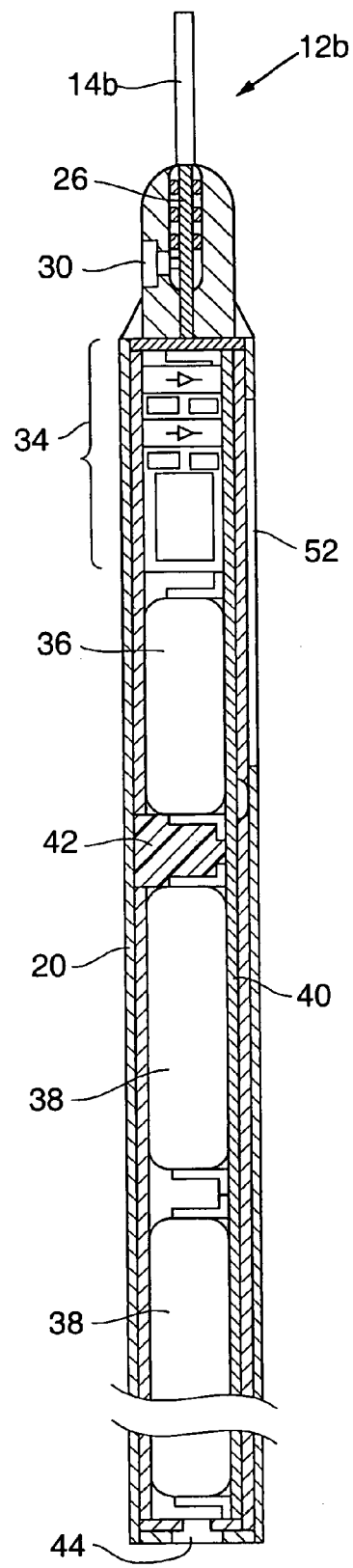
FIG. 3B is a plan view similar to FIG. 3A showing a second embodiment of an intravascular defibrillation and/or pacing device of a type which may be used with the system shown in FIG. 2.

A second example of an arrangement of components for the intravascular defibrillation and/or pacing device is identified by reference numeral 12b and shown in FIG. 3B. Many of the components are the same as those shown in the FIG. 3A embodiment and will not be discussed again in connection with FIG. 3B. This second embodiment differs from the first embodiment primarily in that the electronic components 34 are included within a single area of the enclosure 20. This configuration may be used, for example, when the device is intended only for performing pacing functions (and thus lacks the relatively noisy charging circuitry found in the defibrillation circuitry), or if isolation of the type shown in the FIG. 3A embodiment is not necessary to prevent noise from the charging circuit from interfering with the sensing circuits.

Figure 3C:
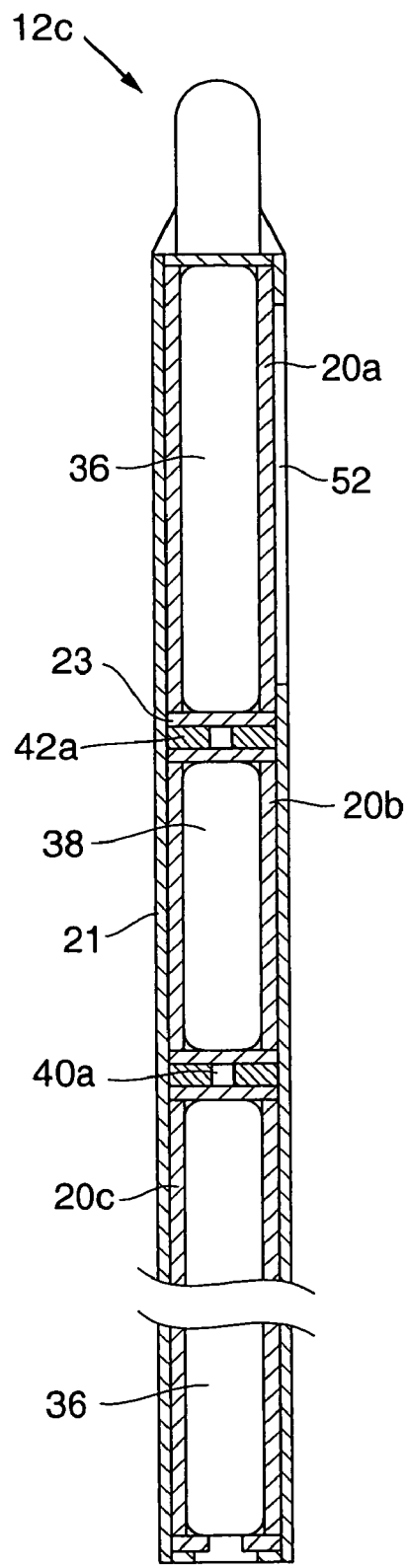
FIG. 3C is a plan view showing a third embodiment of an intravascular defibrillation and/or pacing device of a type which may be used with the system shown in FIG. 2.
Figure 3D:
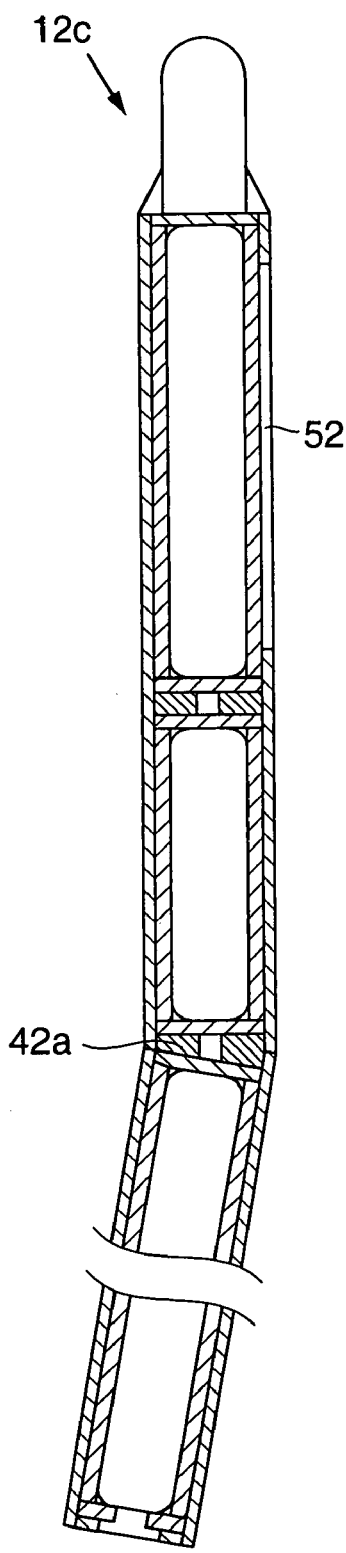
FIG. 3D is a plan view similar to FIG. 3C illustrating bending of the device.

One variation on the FIGS. 3A and 3B embodiments is the device 12c shown in FIGS. 3C and 3D. In device 12c, each segment may be separately enclosed by its own titanium (or similar) enclosure 20a, 20b, 20c. The components within the enclosures 20a, 20b, 20c are electrically connected by flex circuits 40a, and the enclosures are connected using a flexible material such as silicone rubber filler to form hinge zones 42a. FIG. 3D illustrates bending of the device 12c at one of the hinge zones.

Figures 4A, 4B:
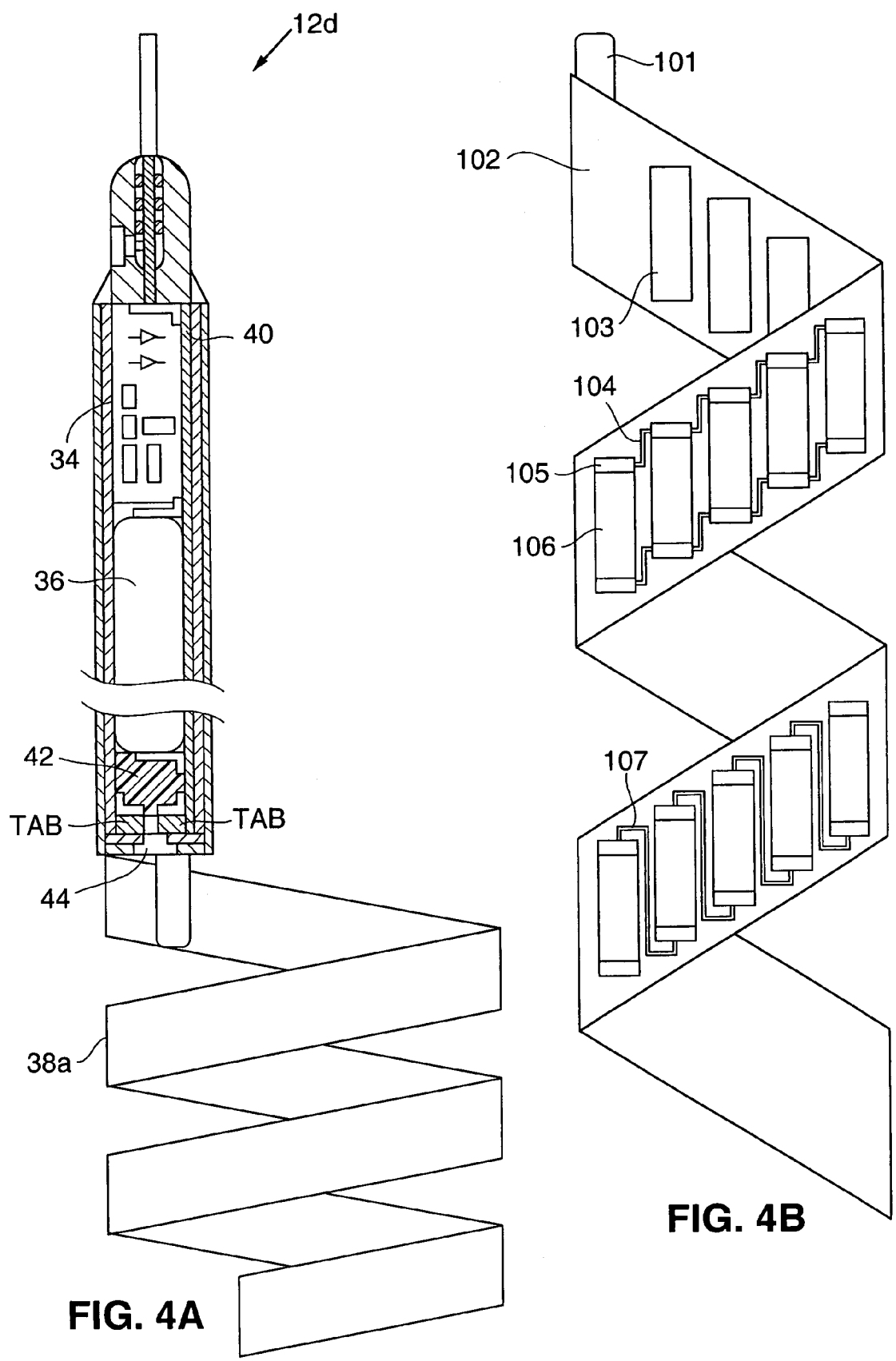
FIG. 4A is a plan view showing a fourth embodiment of an intravascular defibrillation and/or pacing device of a type that may be used with the system shown in FIG. 2.
FIG. 4B is a plan view showing the ribbon portion of the fourth embodiment.

A fourth embodiment of an intravascular defibrillation and/or pacing device is identified by reference numeral 12d and shown in FIG. 4A. Many of the components are the same as those shown in the FIGS. 3A and 3B embodiments and will not be discussed again. The FIG. 4A embodiment differs from the prior embodiments largely in the configuration of the capacitor 38a, which takes the form of a coiled ribbon mechanically coupled to the proximal end of the device 12d (or to a more distal location) and electrically coupled to the circuit interconnect 40. The coiled ribbon may take the form of a flex circuit of the type described in connection with FIG. 4B below, or it may be formed of layers of capacitor material overlaying one another to form the ribbon itself.

Prior to implantation, the capacitor 38a is compressible to a streamlined condition for introduction into the body. For example, it may be placed within a delivery sheath or it may retained in a streamlined position by winding the ribbon against the mandrel and retaining it with a shorter sleeve, suture or wire etc. As yet another example, proximal tension may be imparted on the ribbon by pulling the ribbon in the longitudinal direction, thereby elongating the ribbon while reducing its overall width, much like pulling on a coiled telephone wire. Once positioned within the vessel at the appropriate site for implantation, the capacitor is released from the compressed position and springs to an expanded position within the vessel, as further discussed in the section entitled "System Implantation" below.

Although the ribbon is described as being a capacitor, it should be appreciated that a different subset of the device components may be provided in the form of a ribbon-like structure or circuit. For example, the capacitor may be similar to the capacitors 38 shown in FIGS. 3A and 3B, and the device's battery may instead be formed in the coiled ribbon configuration. In yet another variation, the coiled ribbon may instead be an antenna for transmitting signals alerting a physician to the occurrence of an arrhythmia, and both the capacitor and battery may take the forms shown in FIGS. 3A and 3B, or some alternate form.

FIG. 4B is an enlarged view of the ribbon 102 used for capacitor 38a of FIG. 4A. The ribbon 102 is a coiled flex circuit electrically connected to the rest of the device 12d by tab 101. Discrete capacitor segments 106 are preferably arranged in a stepped pattern on the ribbon surface and may be applied using spray-on/lithographic techniques or other means. Segments 106 have terminals 105 that may be connected in parallel using parallel connections 104, or in series using series connections 107 as needed. The segments 106 may be on the exterior surface of the ribbon 102, and/or there may be additional segments or related components 103 (including integrated circuit components, passive circuitry components, microprocessor components etc.) on the interior surface of the coil.

It should also be noted that the entire device (including the capacitors, batteries, microprocessor, electronics, etc) may take the form of a coiled ribbon flex circuit, with the components being located on the exterior or interior surface of the ribbon and with the leads coupled to the ribbon.

The device 12 is preferably able to communicate via wireless telemetry to an instrument outside of the patient's body. This is commonly referred to as device interrogation and/or programming and allows the physician to monitor the state and performance of the device. It also allows the physician to reconfigure the device in the case of programmable settings.

The circuitry used for device interrogation and/or programming can be included in all of the device embodiments, with the device telemetry antenna either encapsulated within the device enclosure or as part of the ribbon component set. The circuitry may include a circuit that will respond in the presence of a magnetic field, which is a feature also known in the implantable device industry. Either of these communication means, or both, are intended to allow the device to communicate the device's status to the physician. For example, the status information may include the state of the battery system, and whether or not a therapeutic energy delivery had occurred or not. The communication might also identify the parameters the device used, including a stored electrogram, to allow reconstruction of the delivery episode by the instrument. The telemetry feature may also be used to program certain features governing function of the device, such as the threshold heart rate in beats per minute which, when detected by the device, will cause the device to provide appropriate energy therapy.

Referring again to FIG. 2, the system 10 further includes a mechanism for retaining device 12 in the patient's vasculature, such as in the superior vena cava 3a, inferior vena cava 3b, or the left or right subclavian 2a, 2b (see FIG. 1). Although various means may be used to retain the device within the vasculature, one example of a retention device is a tubular retention sleeve or anchor 16 as shown in greater detail in FIGS. 5A and 5B. The retention device is described as a separate component from the device 12, but it will be appreciated that the anchor 12 or other retention device may be integral with the device 12.

The anchor 16 may include features that give some structural stability to cause the anchor to radially support the device against a vessel wall. For example, a mesh or other framework 46 (FIG. 5B) formed of shape memory (e.g. nickel titanium alloy, nitinol or shape memory polymer) elements or stainless steel wires may be used. The anchor 16 is preferably provided with a smooth polymeric barrier 48 that is both anti-proliferative and anti-thrombogenic and that thereby prevents endothelial growth and thrombus formation on the anchor. Examples of materials for the polymeric barrier include, but are not limited to ePTFE, or other fluoropolymers, silicone, non-woven nylon, or biomimetic materials.

The polymeric barrier 48 is preferably formed by layers of barrier material on the interior and exterior surfaces of the framework, although it will be appreciated that the framework 46 and barrier 48 may be combined in a variety of ways to prevent thrombus formation and endothelialization on the anchor walls. As one alternative (or in addition to the polymeric barrier), the anchor material could include surfaces for eluting non-coagulative, anti-platlet (e.g. IIBIIIA glycoprotein receptor blockers), anti-proliferative, and/or anti-inflammatory substances.

Figure 5A:
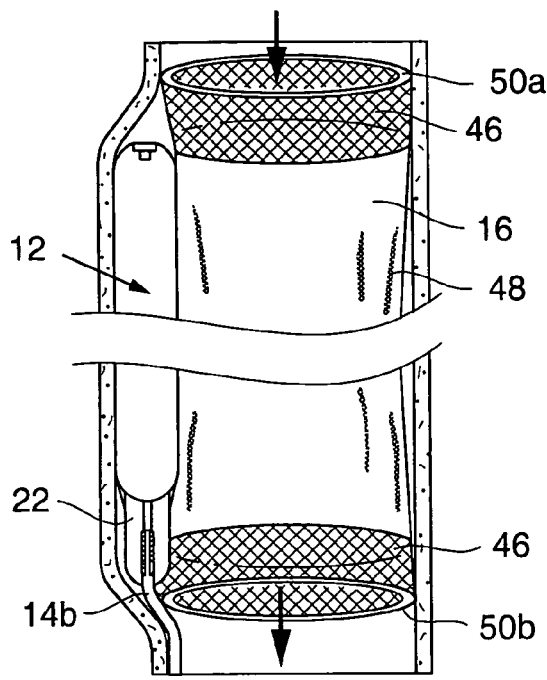
FIG. 5A is a perspective view schematically illustrating use of an anchor to anchor an intravascular defibrillation and/or pacing device within a vessel.

The framework 46 may extend through the entire length of the anchor, or it may be included in only a portion of the anchor, such as at the proximal and distal end regions as shown in FIG. 5A, leaving the intermediate region between them with no structural reinforcement. This arrangement may be preferable in that is allows the intermediate region to conform to the surface of the device 12 during use. As another alternative, the intermediate region may include some structural reinforcement in the intermediate region, 49 between the more rigid proximal and distal framework regions 46, but less than is provided in the proximal and distal regions 46 so as to allow some conformability to the device surface.

During implantation, the anchor 16 is compressed to a streamlined positioned for passage through the vasculature. The anchor 16 may be inserted into a positioning sheath to facilitate movement through the vasculature.

Typically the anchor will be introduced after the device has been positioned at a desired location within the vessel, although if the anchor and device are integral components they will be implanted simultaneously. The anchor is advanced to a position adjacent the device, released from the sheath (if used) and expanded to a radially expanded position as shown in FIG. 5A. The anchor may self-expand and/or it may be expanded using an inflation tool such as a balloon passed into the anchor's central lumen and subsequently inflated. When the anchor is expanded, its radial forces engage the device 12 and secure the device 12 against the vessel wall. As shown, the force of the anchor against the device may cause the vessel to bulge outwardly. Blood flowing through the vessel passes through the tubular interior of the anchor as indicated by arrows in FIG. 5A. Because the device 12 occupies the bulge in the vessel, the presence of the device causes minimal (if any) obstruction to blood flowing through the vessel.

It is desirable to minimize passage of blood between the anchor 16 and the device 12 so as to minimize the chance of thrombus formation and endothelialization around the device 12. For this reason, the rims 50a, 50b surrounding the anchor's proximal and distal openings are preferably designed to make sealing contact against the surrounding vessel tissue (and against the lead 14b) as shown in FIG. 5A so as to direct all blood flow into the interior of the anchor. For example, rims 50a, 50b may be formed of a thicker and more pliable material such as silicone or polyurethane-siloxane, or the rims may be supplemented with compliant members that seal against the lead and surrounding tissue. As another example, a swellable hydrogel which expands when placed in contact with fluids including blood, may be included on the anchor's ends to optimize sealing. Ideally, these barriers will form a seal with the adjacent tissue, however it is sufficient that the barriers prevent a substantial amount of blood from passing between the exterior of the anchor and the device, without necessarily forming an impermeable seal.

As will be described below, additional anchoring devices such as anchor 16a (FIG. 2) similar to the anchor 16 may also be used to anchor leads within the vasculature.

Figure 5C:
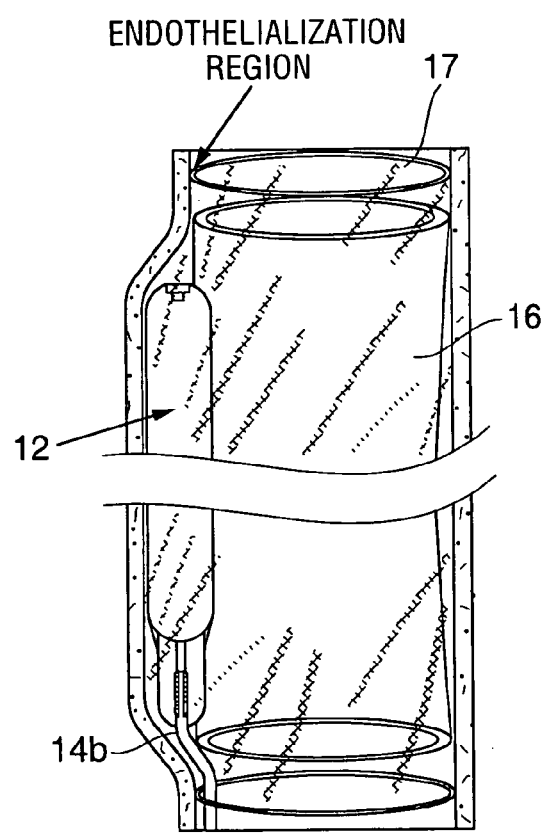
FIG. 5C is a perspective view similar to FIG. 5A but further illustrating use of a liner within the vessel.
Figure 5B:
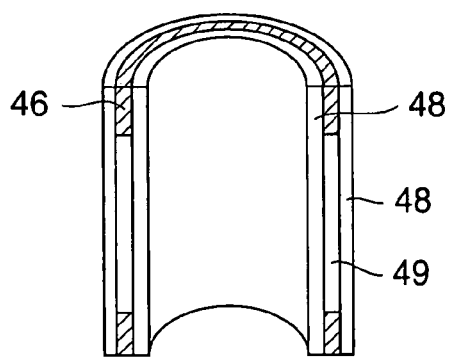
FIG. 5B is cross-sectional perspective view showing a portion of the anchor of FIG. 5A.

As discussed, it is desirable to minimize endothelial growth onto the anchor, since endothelial growth onto the anchor 16 can make it difficult to separate the anchor and device 12 from the vessel tissue during explantation. Referring to FIG. 5C, a tubular liner 17 may be deployed within the vessel prior to implantation of the device 12 and anchor 16. Liner 17 may be similar in design to the sheath 16, but is preferably longer than either the device 12 or anchor 16 so that the liner contacts the vessel wall but the device and anchor 16 do not. If used with the FIG. 4A embodiment of the device 12d, which includes coiled ribbon 38a, the liner 17 is preferably longer than the combined length of the enclosure 20 and coil 38a. The liner 17 helps to reduce the risk of trauma to the vessel tissue during explantation of the device and/or anchor 16.

During implantation, the liner 17 is deployed in the desired anatomic location before the device is moved into place. The steps for deploying the liner 17 may be similar to those described above for depolying the anchor 16. Once the liner 17 is in place, the device is deployed, followed by the anchor 16, in the same manner as described elsewhere. Over time the liner may become endothelialized, particularly at its edges. However, the endothelial growth is self limiting to the edge or rim of the liner due to increasing distance from a sustaining blood supply and should not reach the inner retaining sleeve 16. Thus, when it is necessary to explant the device 12 for servicing (such as to replace a battery for example) the inner anchor 16 may be grabbed by a surgical instrument with the outer liner 17 acting as a protective layer for the vessel. The liner 17 may be left in place following removal of the anchor 16 and device 12. If the device 12 (or a replacement) is to be later re-implanted, it may be returned to its original location within the liner 17.

In an alternative implantation method, the device 12 may be "sandwiched" between the liner 17 and anchor 16 before implantation by placing the device inside the liner, then placing the anchor in a compressed position within the liner, and then expanding the anchor to engage the device between the sleeve and anchor. The three components are then compressed into a positioning sheath and introduced as described elsewhere.

Applications

System 10 (FIG. 2) is adaptable for use in a variety of applications, including single chamber atrial or ventricular pacing, dual chamber (atrial and ventricular) pacing, bi-atrial pacing for the suppression of atrial fibrillation, bi-ventricular pacing for heart failure patients, ventricular defibrillation for ventricular tachycardia or ventricular fibrillation, and atrial defibrillation for patients suffering from atrial fibrillation. The system may be adapted to perform multiple functions for use in combinations of these applications. The system may be implanted for permanent use, or it may be implanted for temporary use until more permanent interventions can be used FIGS. 6A through 12 illustrate some of these applications as well as some configurations of the system that are suitable for each application. The defibrillation and/or pacing device embodiments 12a, 12b, 12c, and 12d shown in FIGS. 3A-4B and the anchor 16 of FIG. 5A may be used for the described applications, although numerous alternative forms of defibrillation and/or pacing devices and anchoring mechanisms may also be used without departing from the scope of the invention. Moreover, although each of the described applications involves placement of the device in the venous system, it should be noted that it may alternatively be placed within the arterial system (such as to allow generation of defibrillation vectors from the aortic arch to the descending aorta) if warranted.

FIGS. 6A and 6B show components of the FIG. 2 system 10 as used as an implanted cardioverter defibrillator (ICD) for treatment of ventricular fibrillation. In this configuration, device 12 is anchored in the inferior vena cava 3b using anchor 16.

A defibrillation lead 14b is included with the system 10 and is anchored within the patient's left subclavian. An anchor 16a similar to the anchor 16 may be used for this purpose. Anchor 16a may be smaller than anchor 16 since the lead 14b it anchors is relatively lighter than the device anchored by anchor 16, and because the anchor 16d is positioned within the smaller-diameter left subclavian.

As discussed previously, the lead 14b may include a coiled section 100 as shown in FIG. 6B to permit elongation of the effective length of the lead in response to longitudinal tension.

Lead 14b includes a high voltage electrode surface 54 through which the defibrillation pulse is delivered. During defibrillation, the defibrillation shock vector flows between electrode surface 54 on the lead and the electrode surface 52 on the device 12 as indicated by arrows. Orienting the electrode 52 towards the heart as shown in FIG. 6A contributes to focusing of the defibrillation current. Moreover, because the anchor 16 functions as an insulator, it helps to minimize conduction of the high voltage current away from the heart and thus also facilitates current focusing. Configuring the system to focus the current can reduce the amount of defibrillation energy needed to defibrillate the patient, since less energy is lost to surrounding tissue, and allows a smaller capacitor to be used within the system. This is beneficial in that in reduces the overall size of the device 12 and further ensures that the device profile will not interfere with blood flow within the vessel.

Although electrode surface 52 is shown positioned towards one side of the device, it may take other forms. For example, the electrode surface may instead extend around the device body to form a band. Focusing is facilitated in this embodiment by positioning the anchor 16 against the side of the device that is furthest from the heart (as is also done in the FIG. 6A application), so as to thereby minimize conduction of the high voltage current from the electrode 52 away from the heart.

In the FIG. 6A application, electrical activity of the heart may be sensed between the high voltage electrode 54 on the lead 14b and the electrode 52 on device 12. Device 12 may alternatively include one or more sensing electrodes (not shown) on its surface for detecting electrical activity of the heart.

Figure 7:
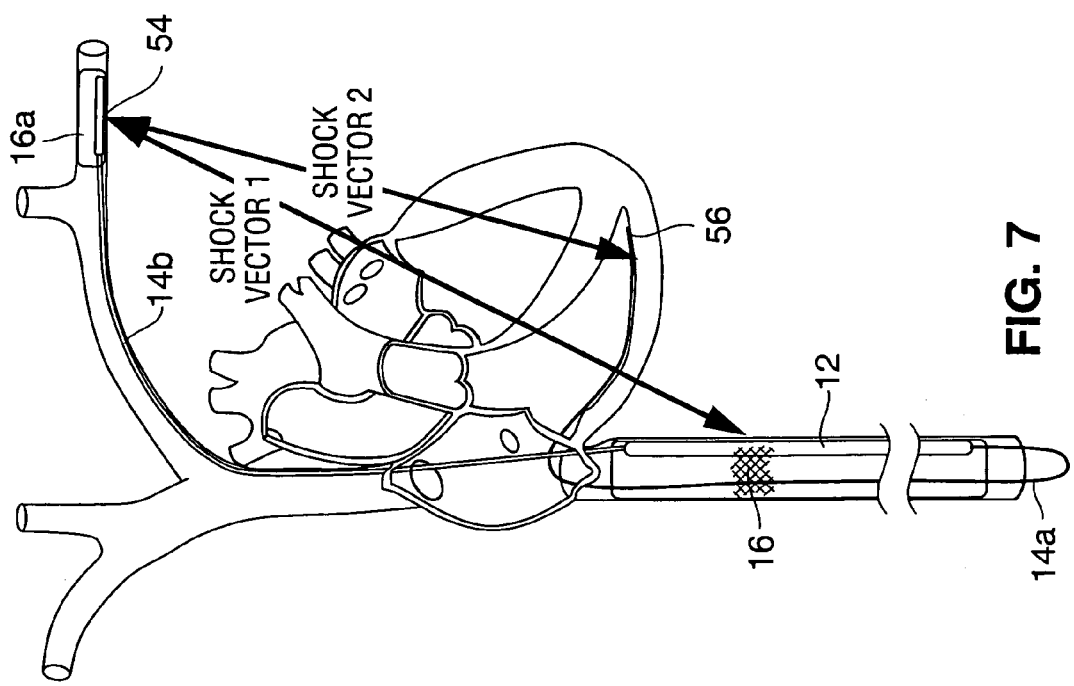
FIG. 7 schematically illustrates a second application of an intravascular defibrillation and/or pacing system.

FIG. 7 illustrates a second application for the FIG. 2 system 10. This application is similar to the first application in that it uses the device 12 as an implantable cardioverter defibrillator ("ICD"), but it further includes a pacing lead 14a positioned in the right ventricle. Pacing lead 14a may be a conventional lead, which includes one or more sensing and pacing electrodes 56. For example, a bi-polar lead of a type commonly used for ICD's and pacemakers may be used, in which case sensing could be carried out between two spaced-apart electrodes on the lead. If a smaller lead is desired, it may be provided with a single sensing electrode and sensing could be accomplished between the single electrode and an exposed electrode (see electrode 52, FIG. 6) on device 12. It should be noted that although FIG. 7 shows the defibrillation lead 14b and the sensing lead 14a extending from opposite ends of the device 12, both leads may instead extend from one end of the device.

For defibrillation, the FIG. 7 arrangement may be configured such that the shock vector applied to the heart extends from the defibrillation electrode 54 and a location on the device 12 as indicated by arrows. Alternatively, a high voltage lead may be used as the lead 14a, in which case the device could be configured to apply the shock vector between electrode 54 and the electrode 56 on lead 14a.

Figure 8:
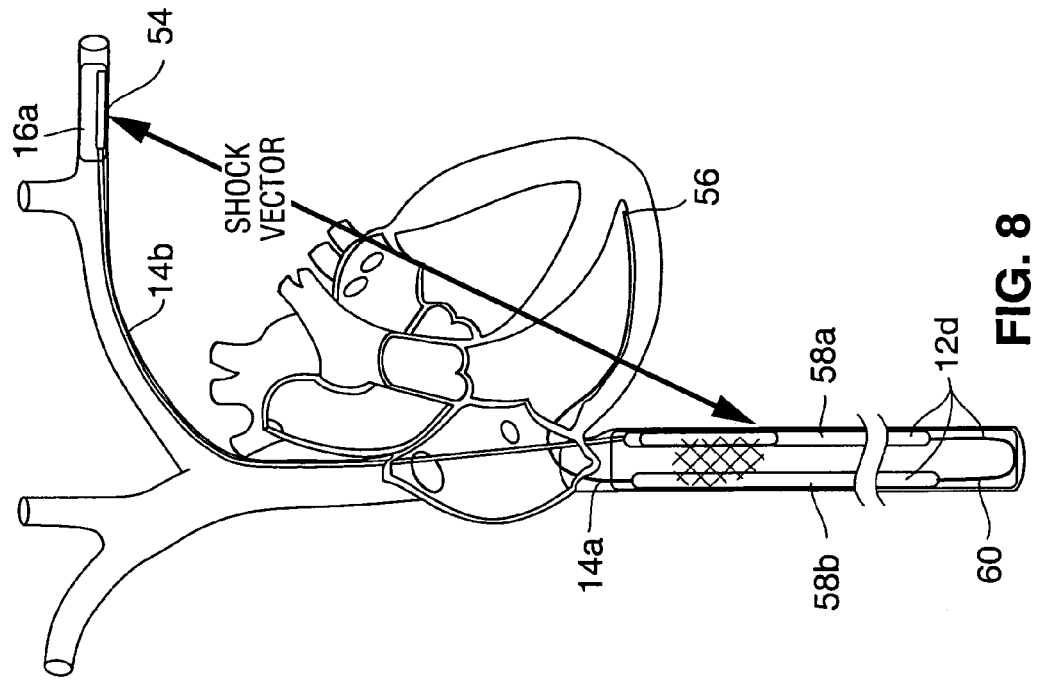
FIG. 8 schematically illustrates a third application of an intravascular defibrillation and/or pacing system.

A third application is shown in FIG. 8. The third application is largely similar to the second application, but uses a device 12d that is divided into two separate housings 58a, 58b. For example, housing 58a may contain the components needed for defibrillation (e.g. the electronics, capacitors and the batteries) while housing 58b contains the components associated with the sensing function (e.g. the electronics and associated batteries).

Dividing components into separate packages may provide several advantages. First, it allows for use of an anchor having a shorter longitudinal dimension, which facilitates placement of the anchor in a location where it will not obstruct blood flow into/from peripheral vasculature. The separate packages can be anchored by a single anchor as shown in FIG. 8, or the packages may be positioned in series in the vessel and separate anchors may be used for each.

Second, battery life may be optimized by using separate batteries for pacing and defibrillation—thereby supporting each function with a battery type most suitable for the function and optimizing battery life. For example, one or more batteries having chemistries of the type used for pacemaker batteries (typically lithium iodide batteries which can come in very small sizes due to their high energy density) may be used for the low current pacing and sensing function. Batteries having chemistries similar to typical implantable defibrillator batteries, which are faster charging and which can produce larger current surges than pacing batteries, (e.g. LSOV) may be separately used for the defibrillation function. Third, as discussed previously, physically isolating the sensing components from the defibrillation components can improve electrical sensing performance during device charging.

An inter-device cable 60 provides communication between the components of the housings 58a, 58b, although other forms of communication (e.g. wireless RF, infrared, acoustic, telemetric) might also be used. As yet another alternative, the structural framework 46 of anchor 16 (FIG. 5B) may be used as a conductor or antenna for this purpose.

Figure 9A:
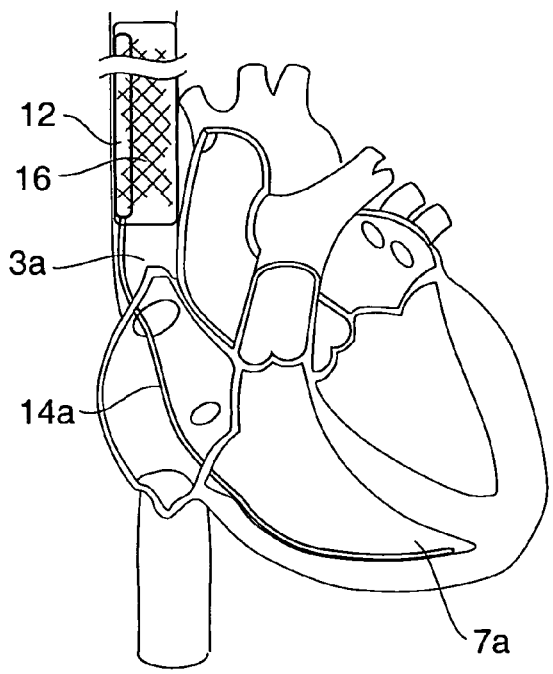
FIG. 9A schematically illustrates a fourth application of an intravascular defibrillation and/or pacing system.
Figure 9B:
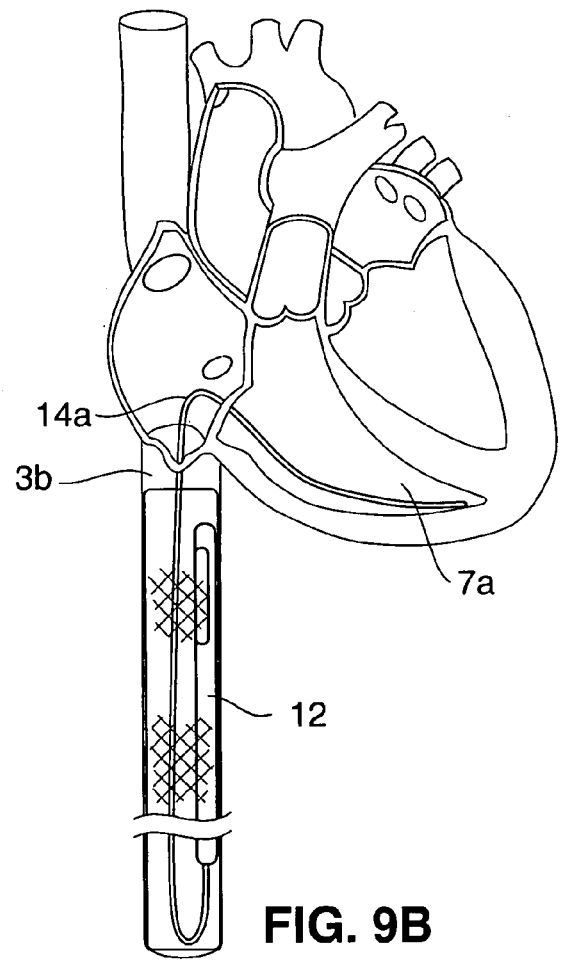
FIG. 9B schematically illustrates a variation of the fourth application of FIG. 9A.

FIG. 9A shows an alternative application in which the FIG. 2 system 10 is used for single-chamber ventricular pacing. As shown, device 12 is anchored by anchor 16 in the superior vena cava 3a. The distal end of pacing lead 14a is positioned in the right ventricle 7a. As shown in FIG. 9B, the device 12 and anchor 16 may alternatively be positioned within the inferior vena cava 3b. As yet another variation on this application shown in FIG. 9C, a leadless device 12e having a surface pacing electrode 64 is itself positioned within the right ventricle 7a.

Figure 10A:
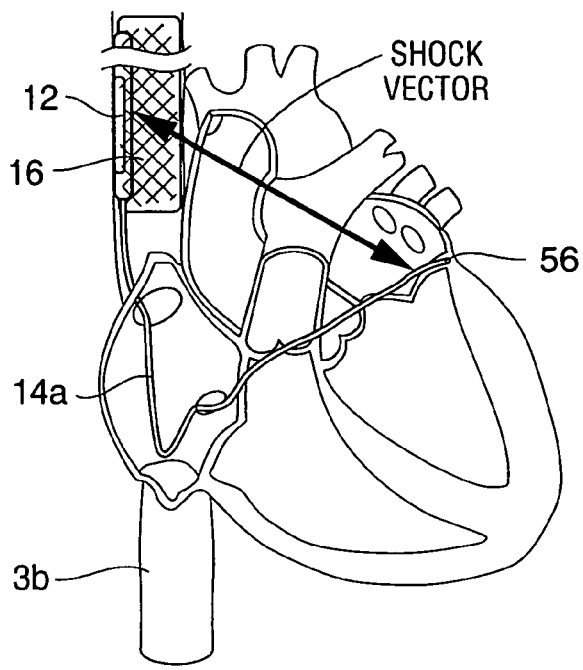
FIG. 10A schematically illustrates a fifth application of an intravascular defibrillation and/or pacing system.
Figure 10B:
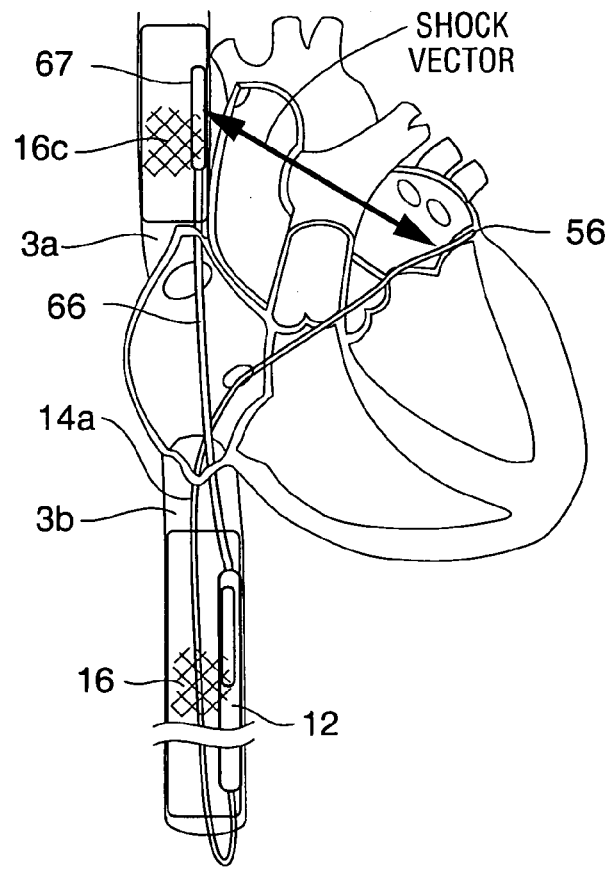
FIG. 10B schematically illustrates a variation of the fifth application of FIG. 10A.

FIG. 10A shows an alternative application in which the FIG. 2 system 10 is used as an implanted cardioverter for atrial fibrillation, with device 12 anchored by anchor 16 in the superior vena cava 3a, and a sensing/pacing lead 14a having electrode 56 extending through the coronary sinus. During cardioversion, the shock vector extends between an exposed electrode on device 12 and electrode 56 within the coronary sinus. FIG. 10B shows an alternative to the FIG. 10A configuration for atrial fibrillation, in which the device 12 may be positioned in the inferior vena cava 3b and a high voltage electrode lead 66 placed in the superior vena cava 3a and supported by another anchoring device such as anchor 16c. In this variation, the cardioversion shock vector extends between a distal electrode on pacing lead 14a and a high voltage electrode 67 on lead 66.

Figure 11A:
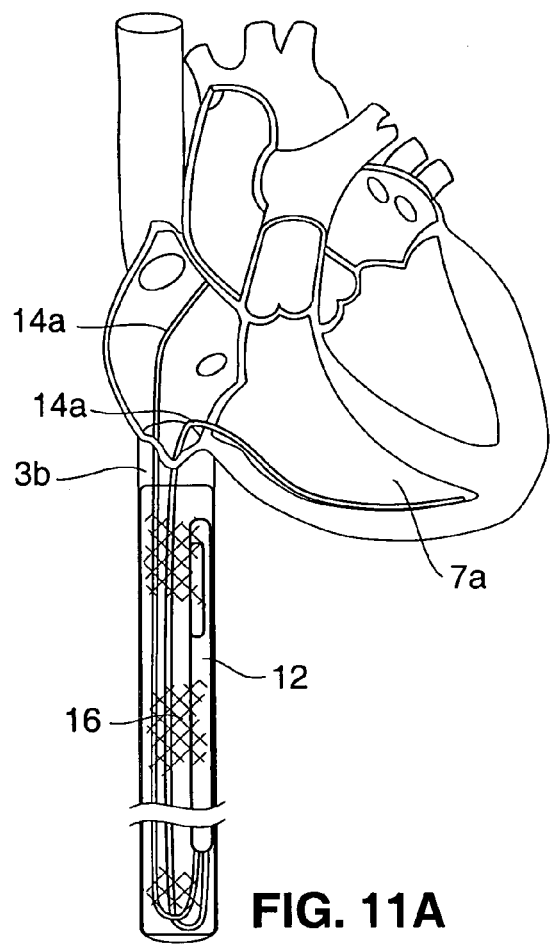
FIG. 11A schematically illustrates a sixth application of an intravascular defibrillation and/or pacing system.
Figure 11B:
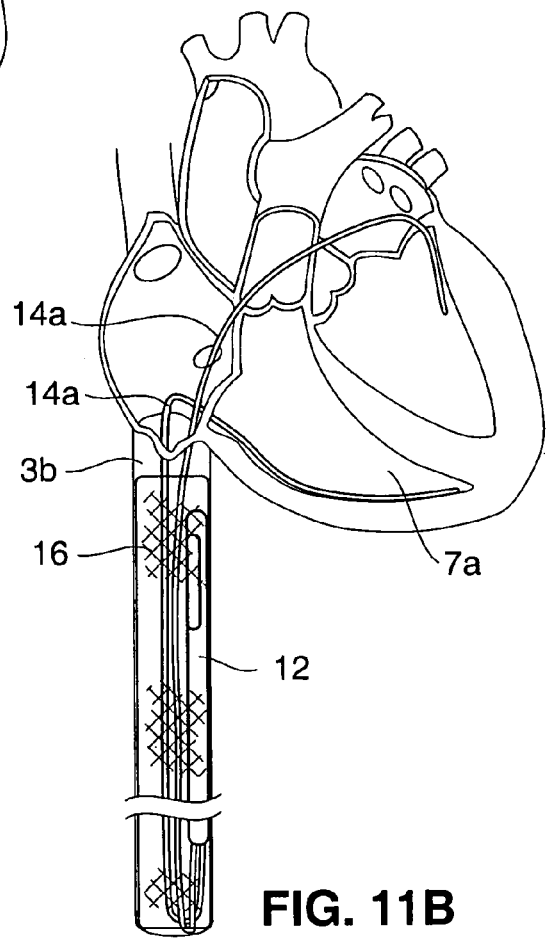
FIG. 11B schematically illustrates a variation on the sixth application of FIG. 11A FIG. 12 schematically illustrates a seventh application of an intravascular defibrillation and/or pacing system.

FIGS. 11A and 11B shows use of the FIG. 2 system 10 as a dual chamber pacer having two pacing leads 14a. Device 12 is anchored in the inferior vena cava 3b using anchor 16. The FIG. 11A embodiment is shown positioned for pacing the right and left ventricles. Ventricular pacing is performed by one of the pacing leads 14a which is positioned in the right ventricle 7a as shown, and atrial pacing is performed using another pacing lead 14a that is positioned in contact with the intra-atrial septum. The FIG. 11B embodiment is shown positioned for bi-ventricular pacing, with each of the pacing leads 14a positioned in one of the ventricles.

Figure 12:
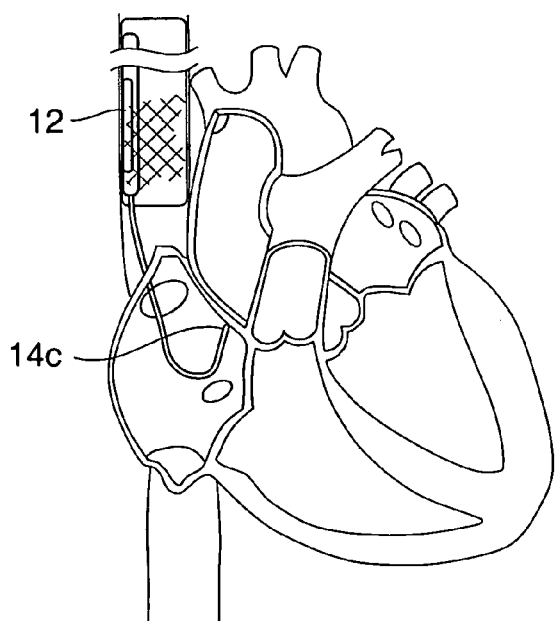
Figure 16:
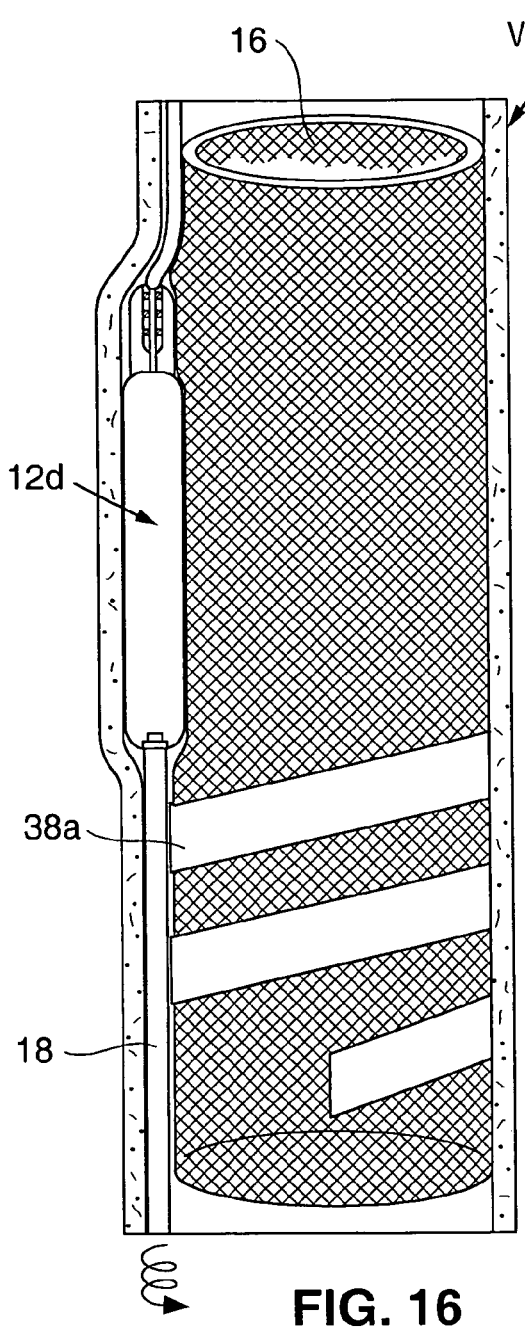

FIG. 12 shows use of the FIG. 2 system 10 for atrial pacing. In this application, an atrial J-lead 14c is coupled to the device 12 and is positioned in contact with the intra-atrial septum.

System Implantation

The system 10 may be implanted using a variety of techniques. Six examples of these techniques will next be described. Although most of the examples describe implantation through the femoral vein, it should be understood that alternate approaches (e.g. through the subclavian, or through both femoral veins) without departing from the scope of the invention.

First Example

The first implantation method will be described with respect to the device 12d of FIGS. 13A and 13B, but is appropriate for implantation of the other devices described herein, as well.

According to a first example of an implantation method, a small incision is formed in the femoral vein and an introducer sheath is inserted through the incision into the vein to keep the incision open during the procedure.

Next, positioning mandrel 18 is attached to the proximal end of the device 12d. Device 12d is advanced into the introducer sheath, and pushed using mandrel 18 (preferably under fluoroscopic visualization) to the desired location. As shown in FIGS. 13A and 13B, a portion of the device may be enclosed within a sleeve 68, particularly for embodiments having expandable components such as ribbon coil 38a which must be compressed to a streamlined position for passage through the vessel. As shown in FIG. 13B, the ribbon coil 38a is released from the sleeve 68 once the device 12 has been advanced by mandrel 18 to the desired position, and the ribbon coil 38a springs to its expanded condition in contact with the vessel walls once the device 12d is released from the distal end of the catheter. The expanded coil may take the form shown in FIG. 13B, or it may spiral into overlapping layers to shorten its longitudinal dimension. A balloon may be expanded within the coil if needed for full expansion.

FIGS. 14-17 illustrate one method for anchoring the device using anchor 16. Although these figures illustrate anchoring of device 12d, they are equally applicable to deployment of other devices within the vasculature, including the devices 12, 12a, and 12b and 12c.

FIG. 14 shows the device 12d of FIG. 4A (attached to mandrel 18) after it has been advanced into the vessel and after the ribbon coil 38a has been released to the expanded position. Once the device 12d is in the desired position, a sheath 62 with the anchor 16 inside it is positioned in parallel with the device 12d while the device 12d is held in place using the mandrel 18. The sheath 62 is withdrawn as shown, releasing anchor 16 into the vessel. As discussed in connection with FIG. 5A, although the sheath 62 facilitates placement of the anchor, it should be considered optional.

Figure 17:
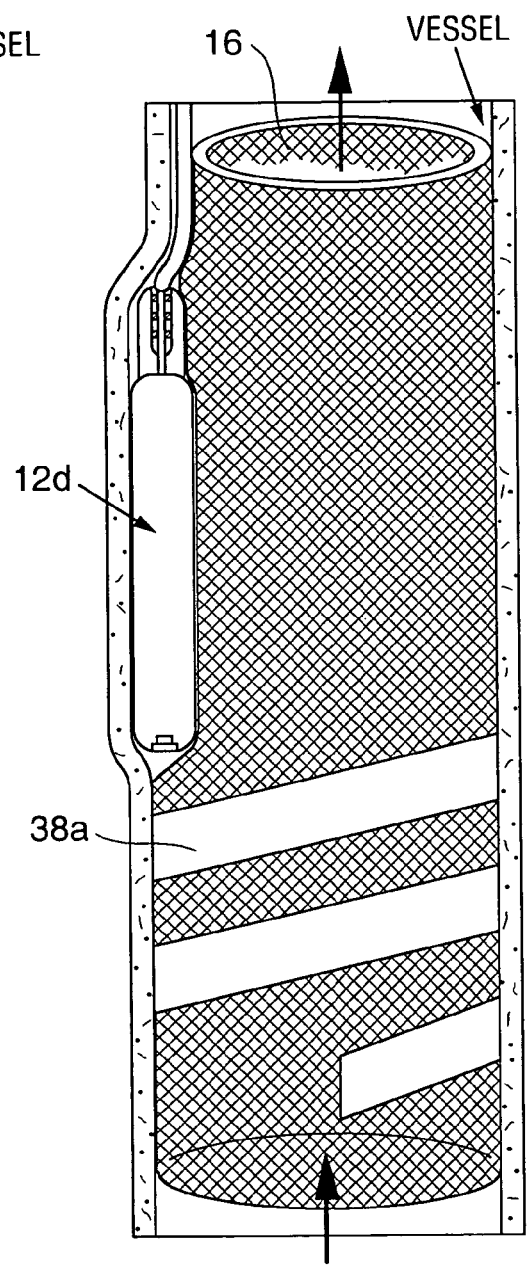

The anchor self-expands or is expanded using an expansion device such as balloon (not shown) inflated within the anchor's central lumen, causing the anchor to radially engage the device 12d against the vessel wall. See FIG. 16. Once the anchor is deployed, the mandrel 18 is detached from the device 12d and withdrawn from the body, leaving the device 12d and anchor 16 in the vessel as shown in FIG. 17.

At this point in the procedure, the device is anchored at the target location. The lead extends from the device and is located outside the body. A steerable guidewire 200 is threaded through the lead 14 near the lead's free end as shown in FIG. 18A and is passed through the introducer sheath into the vein and steered to the desired location. The lead preferably includes a cuff 203 for receiving the guidewire for this purpose. A pusher 204 is then threaded over the guidewire and advanced into contact with the cuff 204. Because cuff 203 is attached to the lead 14, advancing pusher 204 pushes the lead 14 to the target site.

If the target lead location is within a vessel such as the subclavian vein 2b as shown in FIG. 6A, the lead is held in place while a sheath (similar to sheath 62 of FIG. 14) having anchor 16a (FIG. 6A) positioned inside it is moved into position in parallel with a distal portion of the lead. The sheath is withdrawn, releasing anchor 16a into the vessel. The anchor self-expands or is expanded using an expansion device such as balloon (not shown) inflated within the anchor's central lumen, causing the anchor to radially compress the lead against the vessel wall.

If the target lead location is within a chamber of the heart, it may be secured at the target site using conventional securing means such as a helical fixation tip or tines on the distal end of the lead.

If a second lead is to be deployed, the procedure is repeated for that lead.

Second Example

According to a second implantation method, implantation of the system involves first positioning the lead(s) at the desired location (i.e. in a vessel or in a chamber of the heart) and then positioning the device at the appropriate position. As with the first method, lead implantation preferably uses over-the-wire techniques that are widely used for cardiac lead placement. Using the over-the-wire procedure, an introducer sheath is inserted into the femoral vein (or elsewhere in the vasculature) and a steerable guidewire is inserted into the introducer sheath. With the aid of fluoroscopy, the physician guides the wire to the intended lead location. For example, for positioning according to the embodiment of FIG. 6A, the guidewire would be directed to the patient's left subclavian vein 2b, whereas for positioning according to the embodiment of FIG. 9B, the guidewire would be directed to the right ventricle 7a.

Next, the lead (e.g. lead 14b of FIG. 6A or lead 14a of FIG. 9B) is threaded over the wire and pushed by the physician to the desired location. The lead is anchored at the desired location as described in connection with the first exemplary method. If a second lead is to be implanted, the process is repeated for the second lead.

Implantation of the device 12 begins once the distal end of the lead has been anchored at the target location. At this point the proximal end of the lead preferably extends outside the body from the introducer sheath, which remains in the open vein. If the lead is provided as a separate component from the device, the lead is next attached to the device 12.

Next, positioning mandrel 18 (FIG. 2) is attached to the proximal end of the device 12. Device 12 is advanced into the introducer sheath, and pushed using mandrel 18 (preferably under fluoroscopic visualization) to the desired location. Once at the desired location, device 12 is anchored in place using anchor 16 as described in connection with the first example.

The positioning sheath, mandrel, and introducer sleeve are withdrawn from the patient.

Third Example

The third example of an implantation method is similar to the second example, but differs in that the leads and device are simultaneously advanced using the over-the-wire technique. As such, the third example is particularly useful for devices having pre-attached leads.

Figure 18C:
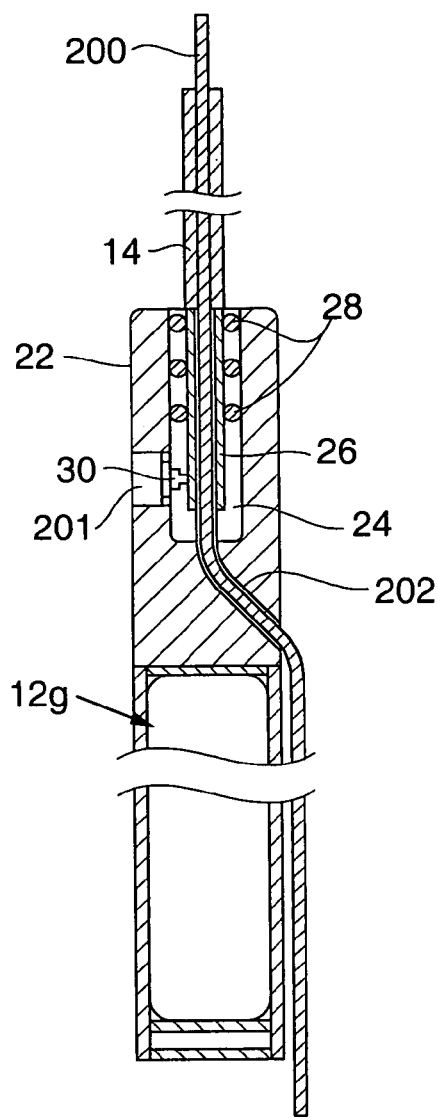
FIG. 18C is a plan view similar to FIG. 18B showing an alternative configuration for receiving a guidewire.

For the third example, the lead and/or device is modified to allow the lead to be advanced over a guidewire even though it is attached to the device. Thus, as shown in FIG. 18B the body of the device 12f may be provided with a bore 202 that receives the same guidewire that also extends through the lead 14. Alternatively, a channel 204 may extend through a portion of the device 12g as shown in FIG. 18C. In this configuration, the guidewire 200 extends through the lead, into the channel 204, and then runs along the exterior of the device 12g. As yet another example, shown in FIGS. 18D and 18E, the lead 14 is modified to include a cuff 203 that receives the guidewire 200 externally of the lead, allowing the guidewire to run alongside the device 12. It should be noted although that FIGS. 18A and 18B show o-ring seals 28 and a set screw 201, these features may be eliminated if the lead and device are provided to be integral with one another.

According to the third example, an introducer sheath is inserted into the femoral vein and a steerable guidewire 200 is inserted into the introducer sheath. The physician guides the guidewire to the intended lead location as described above.

Next, the lead 14 is threaded over the guidewire. If the FIG. 18B configuration is used, the proximal end of the guidewire 200 is threaded through the lead 14 and then passes through the bore in device 12f. If the FIG. 18C configuration is used, the proximal end of the guidewire passes from the lead into channel 204 in the device header, and then exits the device 12g. In either case, the lead is passed into the introducer sheath. The mandrel 18 (see FIGS. 2 and 13A-16) is preferably attached to the device body and used to push the device and lead over the guidewire through the vasculature. Once the lead has reached the desired location, it is anchored at the desired location as described in connection with the first exemplary method. The mandrel 18 is used to maneuver the device to the target device position, and the device is anchored in place using the anchor as described above.

Figure 18D:
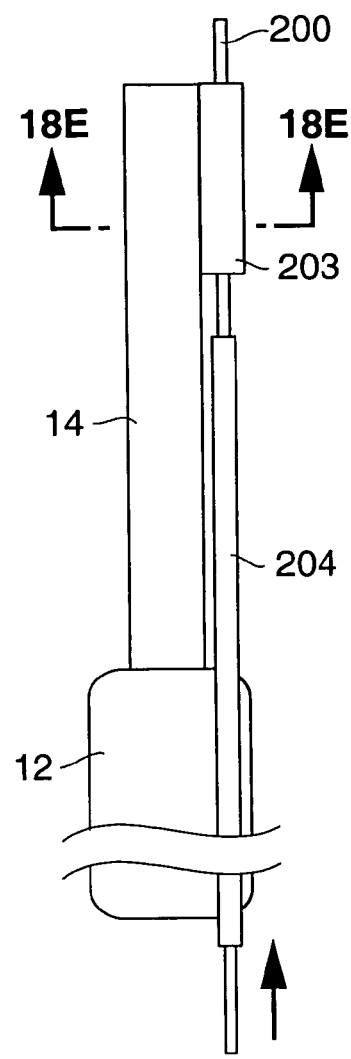
FIG. 18D is a plan view similar to FIG. 18A showing an alternative use of the FIG. 18A device and lead.
Figure 18E:
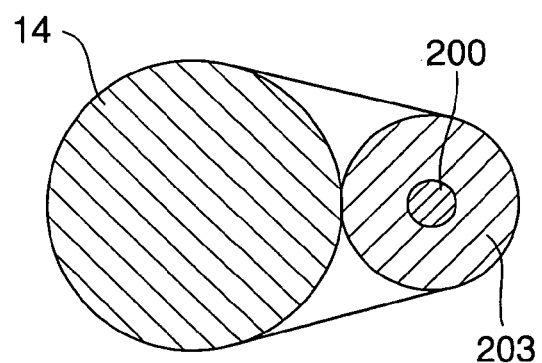
FIG. 18E is a cross-section view of the lead of FIG. 18D taken along the plane designated 18E-18E in FIG. 18D.

If the FIG. 18D configuration is used, the distal portion of the guidewire is threaded through cuff 203, and the mandrel 18 (FIGS. 2 and 13A-16) is attached to the device. The lead is passed into the introducer sheath. A pusher 204 is likewise threaded over the guide wire and advanced into contact with cuff 203. The pusher 204 is further advanced to push the lead to the desired location, at which time the lead is anchored as described. The mandrel 18 is used to advance the device to the appropriate device position, and the device is then anchored in place.

Fourth Example

A fourth example of an implantation method utilizes steps from both the first and third examples and is useful for device configurations such as the FIG. 7 configuration in which leads 14a, 14b extend from opposite ends of the device. According to the fourth example, the lead 14b and device 12 are first implanted using the procedure of the third example, thus leaving the lead 14a extending out the incision in the femoral vein. Lead 14a is then carried into the vein and pushed to the desired position using the procedure of the first example.

Fifth Example

According to a fifth example, incisions are formed in the patient's subclavian 2b and in the femoral vein and introducer sheaths are inserted into each vessel. A guidewire is passed into the introducer sheath in the subclavian, through the right atrium to the superior vena cava and through the introducer sheath in the femoral vein. The guidewire is attached to the lead in a manner similar to that described with the first example, and is then withdrawn at the subclavian incision, thereby pulling the lead into the subclavian and drawing the device 12 into the inferior vena cava. The mandrel 18 may be used as described above to facilitate "fine-tuning" of the device position. The lead and device are anchored as described above.

Sixth Example

Figure 9C:
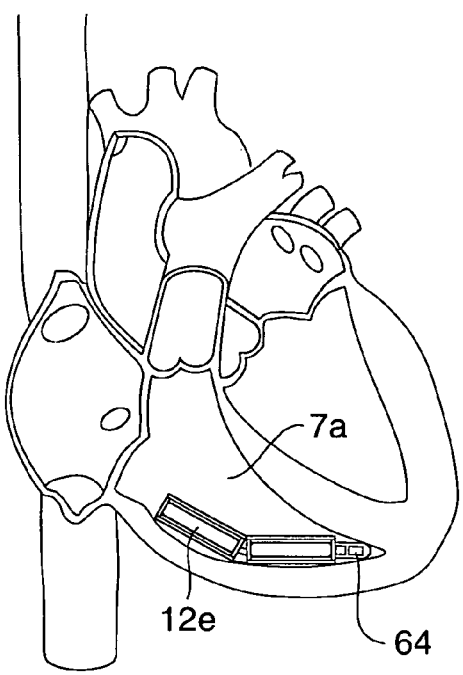
FIG. 9C schematically illustrates another variation of the fourth application of FIG. 9A.

The "leadless" embodiment of FIG. 9C may be provided with a bore or similar means for receiving a guidewire, in which case it may be implanted by first directing a guidewire through the subclavian or inferior vena cava to the right ventricle, threading the device over the guide wire, and then pushing the device (e.g. using mandrel 18) to the ventricle. Alternatively, the device may be advanced through a hollow catheter having its distal end positioned in the right ventricle.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

Any and all patents, patent applications and printed publications referred to above, including those relied upon for purposes of priority, are incorporated herein be reference.

What is claimed is:

1. A method of implanting an intravascular implantable device into a vasculature of a patient, comprising:
    creating an access to a vasculature of a patient;
    introducing a guidewire into the access and advancing the guidewire through the vasculature toward a heart of the patient;
    advancing an intravascular implantable device over the guidewire until it is fully within the vasculature of the patient, the intravascular implantable device including an elongated enclosure containing a battery and electronic components, the enclosure flexible about a longitudinal axis at one or more points;
    anchoring the intravascular implantable device within the vasculature at a target anchor location;
    withdrawing the guidewire from the patient.

2. The method of claim 1, wherein creating the access to the vasculature of the patient comprises creating a femoral access to the vasculature of the patient.

3. The method of claim 1, wherein creating the access to the vasculature of the patient comprises creating a subclavian access to the vasculature of the patient.

4. The method of claim 1, wherein creating the access to the vasculature of the patient comprises making an incision in the vasculature of the patient and inserting an introducer through the incision and into the vasculature.

5. The method of claim 1, wherein the intravascular implantable device further includes a cardiac lead coupled to the elongated enclosure, the method further comprising advancing the lead along the guidewire to a target lead location.

6. The method of claim 5, wherein advancing the lead along the guidewire comprises pushing the lead through the vasculature with a pusher.

7. The method of claim 6, wherein the pusher defines an axial hollow core, and pushing the lead through the vasculature with a pusher further comprises inserting the guidewire through the hollow core of the pusher.

8. The method of claim 5, wherein the lead includes a cuff portion for receiving the guidewire, and the method further comprises inserting the guidewire through the cuff.

9. The method of claim 8, wherein pushing the lead comprises pushing the cuff portion.

10. The method of claim 5, wherein advancing the lead is performed prior to advancing the intravascular implantable device.

11. The method of claim 5, wherein advancing the intravascular implantable device is performed prior to advancing the lead.

12. The method of claim 5, further comprising fixating the lead at the target lead location.

13. The method of claim 1, wherein the enclosure is segmented along the longitudinal axis into modules with one or more hinge zones between adjacent modules, and advancing the intravascular implantable device comprises bending the hinge zones as the enclosure is advanced within the vasculature.

14. A system for implanting an intravascular implantable device into a vasculature of a patient, comprising:
    a guidewire adapted to be passed through an access to a vasculature of a patient and guided through the vasculature of the patient toward a heart of the patient;
    an intravascular implantable device including an elongated enclosure containing a battery and electronic components, the enclosure flexible about a longitudinal axis at one or more points, the device adapted to fit over the guidewire and to be fully inserted into the vasculature of the patient;
    an anchor device for anchoring the intravascular implantable device within the vasculature of the patient at a target anchor location.

15. The system of claim 14, wherein the intravascular implantable device further includes a lead extending from an end of the intravascular implantable device.

16. The system of claim 15, wherein the lead comprises a cuff portion for receiving the guidewire.

17. The system of claim 16, the system further comprising a pusher adapted to push the lead at the cuff portion over the guidewire through the vasculature to a target lead location.

18. The system of claim 14, wherein the enclosure of the intravascular implantable device is segmented along the longitudinal axis into modules with one or more hinge zones between adjacent modules, such that the hinge zones bend as the enclosure is advanced within the vasculature.

19. A method, comprising:
    providing an intravascular implantable device, the intravascular implantable device including an elongated enclosure containing a battery and electronic components, the enclosure flexible about a longitudinal axis at one or more points, the device further including a means for receiving a guidewire; and
    providing a set of instructions for implanting the intravascular implantable device into the vasculature of the patient, the instructions including the steps of:
    introducing a guidewire through an access to the vasculature and advancing the guidewire through the vasculature toward a heart of the patient;
    advancing the intravascular implantable device over the guidewire until the intravascular implantable device is fully within the vasculature of the patient; and
    anchoring the intravascular implantable device within the vasculature at a target anchor location.

20. The method of claim 19, wherein the instructions further include the step of withdrawing the guidewire from the patient.

* * * * *